(12) United States Patent
García López et al.

(10) Patent No.: US 9,181,195 B2
(45) Date of Patent: Nov. 10, 2015

(54) SIGMA RECEPTOR INHIBITORS

(75) Inventors: Mónica García López, Barcelona (ES);
Antoni Torrens Jover,
Terrasa-Barcelona (ES); José Luis Díaz Fernández, Manresa-Barcelona (ES);
Ana María Caamaño Moure, Caruña (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 124 days.

(21) Appl. No.: 13/699,341

(22) PCT Filed: May 26, 2011

(86) PCT No.: PCT/EP2011/058633
§ 371 (c)(1),
(2), (4) Date: Feb. 7, 2013

(87) PCT Pub. No.: WO2011/147910
PCT Pub. Date: Dec. 1, 2011

(65) Prior Publication Data
US 2013/0158029 A1 Jun. 20, 2013

(30) Foreign Application Priority Data
May 27, 2010 (EP) .................... 10382148

(51) Int. Cl.
*C07D 231/12* (2006.01)
*C07D 401/04* (2006.01)
*C07D 413/12* (2006.01)
*C07D 231/14* (2006.01)

(52) U.S. Cl.
CPC ............ *C07D 231/12* (2013.01); *C07D 231/14* (2013.01); *C07D 401/04* (2013.01); *C07D 413/12* (2013.01)

(58) Field of Classification Search
None
See application file for complete search history.

(56) References Cited

U.S. PATENT DOCUMENTS

| 4,337,263 | A | 6/1982 | Techer et al. |
| 6,492,529 | B1 | 12/2002 | Kapadia et al. |
| 6,509,367 | B1 | 1/2003 | Martin et al. |
| 8,193,223 | B2 | 6/2012 | Jagerovic et al. |
| 2003/0144309 | A1 | 7/2003 | Choon-Moon |

FOREIGN PATENT DOCUMENTS

| EP | 0 248 594 A2 | 12/1987 |
| EP | 0 414 289 B1 | 2/1991 |
| EP | 0 445 974 A2 | 9/1991 |
| EP | 0 518 805 A1 | 12/1992 |
| EP | 0 529 973 A1 | 3/1993 |
| EP | 0 431 943 B1 | 7/1998 |
| EP | 1 829 866 A1 | 9/2007 |
| FR | 2 301 250 | 9/1976 |
| JP | 2004-196678 | 7/2004 |
| WO | WO 91/09594 | 7/1991 |
| WO | WO 02/092573 A2 | 11/2002 |
| WO | WO 02/102387 A1 | 12/2002 |
| WO | WO 2004/016592 A1 | 2/2004 |
| WO | WO 2004/017961 A2 | 3/2004 |
| WO | WO 2006/021462 A1 | 3/2006 |
| WO | WO 2007/002559 A1 | 1/2007 |
| WO | WO 2007/079086 A1 | 7/2007 |
| WO | WO 2007/098964 A2 | 9/2007 |
| WO | WO 2007/108517 A1 | 9/2007 |
| WO | WO 2008/108517 A2 | 9/2008 |
| WO | WO 2009/130331 A1 | 10/2009 |

OTHER PUBLICATIONS

Shvidenkom, K.V. et al., "Recyclization Reactions of 2-(1-Benzoylpyrrolidin-2-Ylidene)Malononitrile", 2010, vol. 46, No. 1, pp. 56-60.

Wagaw, S. et al., "A Palladium-Catalyzed Strategy for the Preparation of Indoles: A Novel Entry Into the Fischer Indole Synthesis", J. American Chemical Society, 1998, vol. 120, pp. 6621-6622.

Reaudegnies, R., et al., "Design and synthesis of novel spirocyclopropyl cyclohexane-1,3-diones and -1,3,5-triones for their incorporation into potent HPPD inhibitors", Tetrahedron Letters, 2010, vol. 51, pp. 2741-2744.

Dauben, W., et al., "Organic Reactions at High Pressure Preparation of Wittig Phosphonium Salts at Ambient Temperature", J. Org. Chem., 1984, vol. 49, pp. 4293-4295.

(Continued)

*Primary Examiner* — Kamal Saeed
(74) *Attorney, Agent, or Firm* — Gary J. Gershik; Cooper & Dunham LLP

(57) ABSTRACT

The invention refers to compounds of general formula (I)

having pharmacological activity towards the sigma receptor, to processes of preparation of such compounds, to pharmaceutical compositions comprising them, and to their use for the treatment and or prophylaxis of a disease in which the sigma receptor is involved.

19 Claims, No Drawings

(56) References Cited

OTHER PUBLICATIONS

Beilstein Registry No. 213356, CrossFire Beilstein Database, accessed Oct. 14, 2010.

Hanner, M., et al., "Purification, molecular cloning, and expression of the mammalian sigma$_1$-binding site", Proc. Natl. Acad. Sci. USA, 1996, vol. 93, pp. 8072-8077.

Hartwig, J., "Synthesis, Structure, and Reactivity of a Palladium Hydrazonato Complex: A New Type of Reductive Elimination Reaction to Form C-N. Bonds and Catalytic Arylation of Benzophenone Hydrazone", Angew. Chem. Int. Ed., 1998, vol. 37, No. 15, pp. 2090-2093.

Maryanoff, B.E. and Reitz, A.B, "The Wittig Olefination Reaction and Modifications Involving Phosphoryl-Stabilized Carbanions. Stereochemistry, Mechanism, and Selected Synthetic Aspects", Chem. Rev., 1989, vol. 89, pp. 863-927.

Petrie, C., et al., "A Novel Biotinylated Adenylate Analogue Derived from Pyrazolo[3,4-*d*]pyrimidine for Labeling DNA Probes", Bioconjugate Chem., 1991, vol. 2, pp. 441-446.

Quiron, R., et al., "A proposal for the classification of sigma binding sites", TiPS, 1992, vol. 13, pp. 85-86.

Shen, D.M., et al., "Versatile and Efficient Solid-Phase Syntheses of Pyrazoles and Isoxazoles", Organic Letters, 2000, vol. 2, No. 18, pp. 2789-2792.

Snyder, S., and Largent, B.L., "Receptor Mechanisms in Antipsychotic Drug Action: Focus on Sigma Receptors", Journal of Neuropsychiatry, 1989, vol. 1, No. 1, pp. 7-15.

Vedejs, E., and Peterson, M.J., "Stereochemistry and Mechanism in the Wittig Reaction", Topics in Stereochemistry, 1994, vol. 21, pp. 1-157.

Beilstein Registry No. 710983, CrossFire Beilstein Database, accessed Oct. 14, 2010.

Walker, J.M., et al., "Sigma Receptors: Biology and Function", Pharmacological Reviews, 1990, vol. 42, No. 4, pp. 355-402.

International Search Report issued on Sep. 21, 2011 by the International Searching Authority in connection with International Application No. PCT/EP2011/058633.

Extended European Search report issued on Oct. 22, 2010 by European Patent Office in connection with European Application No. EP 10 38 2148.

O'Brien, C. J., "Recycling the Waste: The Development of a Catalytic Witting Reaction", Agnew. Chem. Int. Ed. 2009, vol. 48, pp. 6836-6839.

SIGMA RECEPTOR INHIBITORS

This application is a §371 national stage of PCT International Application No. PCT/EP2011/058633, filed May 26, 2011, designating the United States and claiming priority of European Patent EP10382148.4, filed May 27, 2010, the contents of all of which are hereby incorporated by reference into this application.

FIELD OF THE INVENTION

The present invention relates to compounds having pharmacological activity towards the sigma (σ) receptor, and more particularly to some pyrazole derivatives, to processes of preparation of such compounds, to pharmaceutical compositions comprising them, and to their use in therapy and prophylaxis, in particular for the treatment or prophylaxis of a sigma receptor mediated disease or condition.

BACKGROUND

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International patent application WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom. The terms aryl and heteroaryl are defined by mention of a number of such substituents.

European patent application EP 0 414 289 A1 generically discloses a class of 1,2,3,4-tetrahydro-spiro[naphthalene-1,4'-piperidine] and 1,4-dihydro-spiro[naphthalene-1,4'-piperidine] derivatives substituted at the piperidine N-atom with a hydrocarbon group alleged to have selective sigma receptor antagonistic activity. The term hydrocarbon, as defined in said patent, covers all possible straight chained, cyclic, heterocyclic, etc. groups. However, only compounds having benzyl, phenethyl, cycloalkylmethyl, furyl- or thienylmethyl or lower alkyl or alkenyl as the hydrocarbon substituent at the piperidine nitrogen atom are specifically disclosed. The compounds are stated to displace tritiated di-tolyl guanidine (DTG) from sigma sites with potencies better than 200 nM. 1'-benzyl-1,2,3,4-tetrahydro-spiro[naphthalene-1,4'-piperidine] is mentioned as a particularly preferred compound.

European patent application EP 0 445 974 A2 generically describes the corresponding spiro[indane-1,4'-piperidine] and spiro[benzocycloheptene-5,4'-piperidine] derivatives. Again the compounds are only stated to displace tritiated di-tolyl guanidine (DTG) from sigma sites with potencies better than 200 nM.

European patent application EP 0 431 943 A relates to a further extremely broad class of spiropiperidine compounds substituted at the piperidine N-atom and claimed to be useful as antiarrhythmics and for impaired cardiac pump function. The said application exemplifies several compounds, the majority of which contain an oxo and/or a sulfonylamino substituent in the spiro cyclic ring system. Of the remainder compounds, the main part has another polar substituent attached to the spiro nucleus and/or they have some polar substituent on the piperidine N-atom. No suggestion or indication of effect of the compounds on the sigma receptor is given.

Patent applications EP 518 805 A and WO 02/102387 describe sigma receptor ligands having piperidine or spiropiperidine structures.

With regard to the chemical structure of the compounds described in the present patent application, there are some documents in the prior art which disclose pyrazole derivatives characterized, among other things, for being substituted by amino alkoxy groups in different positions of the pyrazole group.

U.S. Pat. No. 4,337,263 discloses 1-aryl-4-arylsulphonyl-3-amino propoxy-1H-pyrazoles, wherein the amino group can be constituted by an N-cycle group as morpholine, piperidine or pyrrolidine group. They are used as hypolipemiant or hypocholesteroleminant agents.

Patent FR 2301250 describes similar compounds as those mentioned above, such as 1,4-diaryl-3-aminoalkoxy pyrazoles, wherein the amino group comprises pyrrolidine, piperidine, hydroxypiperidine, morpholine or piperazine derivatives.

Patent application US2003/0144309 refers to pyrazoles with their 3 position substituted by a dimethylaminoethoxy group and present in their 4 position a pyrimidine group. They are used as inhibitors of JNK3, Lck or Src kinase activity.

International patent application WO 02/092573 describes substituted pirazole compounds as inhibitors of SRC and other protein kinases.

International patent application WO 2004/017961 discloses pyrazole compounds wherein the 3 position is substituted by an alkoxy group directly bounded to a cyclic amide, which are used for therapeutically treating and/or preventing a sex hormone related condition in a patient.

U.S. Pat. No. 6,492,529 describes pyrazole derivatives which are used for the treatment of inflammatory diseases. These compounds present in the 5 position a urea group, linked in some cases to a morpholine ethoxy group.

International patent application WO 04/016592 refers to pyrazole compounds for inhibiting protein prenylation which comprises in the 5 position, among others, an alkoxy group directly bonded to a cyclic amide.

However, none of these documents suggests the effect of these compounds on the sigma receptor.

WO 2006/021462 and WO 2007/098964 describe pyrazole derivatives as selective inhibitors of the sigma receptor. These compounds present in the 3 position an alkoxy group.

There is still a need to find compounds that have pharmacological activity towards the sigma receptor, being both effective and selective, and having good "drugability" properties, i.e. good pharmaceutical properties related to administration, distribution, metabolism and excretion.

BRIEF DESCRIPTION OF THE INVENTION

The inventors of the present invention have surprisingly found a family of structurally distinct pyrazole derivatives which are particularly selective inhibitors of the sigma receptor. The compounds present a pyrazole group which are characterized by the substitution at position 3 by an alkyl chain containing an amine at its end and optionally an intermediate oxa moiety.

Therefore, one aspect of the present invention relates to a compound of general formula (I):

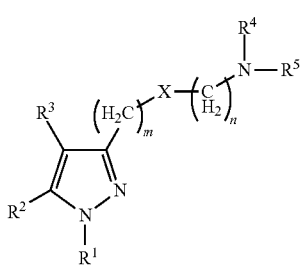

wherein
$R^1$ represents substituted or unsubstituted aromatic or non-aromatic heterocyclyl; substituted or unsubstituted aryl; or substituted or unsubstituted cycloalkyl;
$R^2$ and $R^3$, identical or different, represent a hydrogen atom; F; Cl; Br; I; $CF_3$; OH; SH; $NH_2$; CN; substituted or unsubstituted alkyl; substituted or unsubstituted alkenyl; substituted or unsubstituted alkoxy; substituted or unsubstituted cycloalkyl; substituted or unsubstituted aryl; substituted or unsubstituted, aromatic or non-aromatic heterocyclyl; substituted or unsubstituted cycloalkylalkyl; substituted or unsubstituted arylalkyl; substituted or unsubstituted, aromatic or non-aromatic heterocyclylalkyl; a (C=O)—$R^7$ group; a (C=O)—O—$R^8$ group; a S(O)$_t$—$R^9$ group; or a (C=O)—$NR^{10}R^{11}$ group;
$R^4$ and $R^5$, identical or different, represent a hydrogen atom; substituted or unsubstituted alkyl; substituted or unsubstituted alkenyl; substituted or unsubstituted alkoxy; substituted or unsubstituted cycloalkyl; substituted or unsubstituted aryl; substituted or unsubstituted, aromatic or non-aromatic heterocyclyl; substituted or unsubstituted cycloalkylalkyl; substituted or unsubstituted arylalkyl; substituted or unsubstituted, aromatic or non-aromatic heterocyclylalkyl; a (C=O)—$R^7$ group; a (C=O)—O—$R^8$ group; a S(O)$_t$—$R^9$ group; or a (C=O)—$NR^{10}R^{11}$ group; or
together form, with the nitrogen atom to which they are attached, a substituted or unsubstituted, aromatic or non-aromatic heterocyclyl group;
X represents an oxygen atom or a CH—$R^{12}$ group wherein $R^{12}$ is selected from H, $CH_3$, SH, OH, $NH_2$, $CF_3$, Cl, F, Br, I, and CN;
m is selected from 1, 2, 3 and 4;
n is selected from 1, 2, 3 and 4;
t is selected from 1, 2 and 3;
$R^7$, $R^8$, $R^9$, $R^{10}$ and $R^{11}$, identical or different, represent a hydrogen atom; substituted or unsubstituted $C_{1-6}$ alkyl; substituted or unsubstituted $C_{2-6}$ alkenyl; substituted or unsubstituted $C_{1-6}$ alkoxy; substituted or unsubstituted cycloalkyl; substituted or unsubstituted aryl; substituted or unsubstituted, aromatic or non-aromatic heterocyclyl; substituted or unsubstituted cycloalkylalkyl; substituted or unsubstituted arylalkyl; substituted or unsubstituted, aromatic or non-aromatic heterocyclylalkyl;
or a pharmaceutically acceptable salt, isomer, prodrug or solvate thereof.

Another aspect of this invention refers to the process for the preparation of a compound of formula (I) as defined above, or a salt, isomer or solvate thereof.

Another aspect of this invention refers to a medicament or pharmaceutical composition comprising at least one compound of formula (I) as defined above, or a pharmaceutically acceptable salt, isomer, prodrug or solvate thereof and a pharmaceutically acceptable excipient.

Another aspect of this invention refers to a compound of formula (I) as defined above for use as a medicament, particularly for the treatment and/or prophylaxis of a sigma receptor-mediated disease or condition.

Another aspect of this invention refers to the use of a compound of formula (I) as defined above in the manufacture of a medicament for the treatment and/or prophylaxis of a sigma receptor-mediated disease or condition.

Another aspect of the present invention refers to a method for the treatment and/or prophylaxis of a sigma receptor-mediated disease or condition, the method comprising administering to the subject in need of such a treatment or prophylaxis a therapeutically effective amount of a compound of formula (I) as defined above.

In one embodiment, said sigma receptor-mediated disease or condition is selected from the group consisting of diarrhoea; lipoprotein disorders; migraine; obesity; elevated triglyceride levels; chylomicronemia; dysbetalipoproteinemia; hyperlipoproteinemia; hyperlipidemia; mixed hyperlipidemia; hypercholesterolemia; lipoprotein disorders; hypertriglyceridemia; sporadic hypertriglyceridemia; inherited hypertriglyceridemia; dysbetalipoproteinemia; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive dyskinesia; ischemic stroke; epilepsy; stroke; stress; cancer; psychotic conditions, in particular depression, anxiety or schizophrenia; inflammation; and autoimmune diseases.

In another embodiment, said sigma receptor-mediated disease or condition is selected from the group consisting of pain, preferably neuropathic pain, inflammatory pain or other pain conditions involving allodynia and/or hyperalgesia.

In another embodiment, the compound of formula (I) is used as a pharmacological tool.

These aspects and preferred embodiments thereof are additionally also defined in the claims.

DETAILED DESCRIPTION OF THE INVENTION

In the context of the present invention, the following terms have the meaning detailed below.

"Alkyl" refers to a straight or branched hydrocarbon chain radical consisting of 1 to 12 carbon atoms, containing no unsaturation, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkyl radicals have from 1 to 6 carbon atoms. If substituted by aryl, it corresponds to an "Arylalkyl" radical, such as benzyl or phenethyl. If substituted by heterocyclyl, it corresponds to a "Heterocyclylalkyl" radical. If substituted by cycloalkyl, it corresponds to a "Cycloalkylalkyl" radical.

"Alkenyl" refers to a straight or branched hydrocarbon chain radical consisting of 2 to 12 carbon atoms, containing at least one unsaturation, and which is attached to the rest of the molecule by a single bond. Alkenyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkenyl radicals have from 2 to 6 carbon atoms.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple aromatic ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic (i.e. "heteroaryl") or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —$OR_a$ where $R_a$ is an alkyl radical as defined above having one or more (e.g., 1, 2, 3 or 4) oxygen linkages and from 1 to about 12 carbon atoms or preferably 1 to about 6 carbon atoms, e.g., methoxy, ethoxy, propoxy, etc.

"Amino" refers to a radical of the formula —$NH_2$, —$NHR_a$, or —$NR_aR_b$, optionally quaternized, e.g., methylamino, ethylamino, dimethylamino, diethylamino, propylamino, etc.

"Halogen", "halo" or "hal" refers to bromo, chloro, iodo or fluoro.

References herein to substituted groups in the compounds of the present invention refer to the specified moiety that may be substituted at one or more (e.g., 1, 2, 3 or 4) available positions by one or more suitable groups, e.g., halogen such as fluoro, chloro, bromo and iodo; cyano; hydroxyl; nitro; azido; acyl, such as alkanoyl, e.g. a $C_{1-6}$ alkanoyl group, and the like; carboxamido; alkyl groups including those groups having 1 to about 12 carbon atoms or from 1 to about 6 carbon atoms and more preferably 1-3 carbon atoms; alkenyl and alkynyl groups including groups having one or more (e.g., 1, 2, 3 or 4) unsaturated linkages and from 2 to about 12 carbon or from 2 to about 6 carbon atoms; alkoxy groups having one or more (e.g., 1, 2, 3 or 4) oxygen linkages and from 1 to about 12 carbon atoms or 1 to about 6 carbon atoms; aryloxy such as phenoxy; alkylthio groups including those moieties having one or more (e.g., 1, 2, 3 or 4) thioether linkages and from 1 to about 12 carbon atoms or from 1 to about 6 carbon atoms; alkylsulfinyl groups including those moieties having one or more (e.g., 1, 2, 3 or 4) sulfinyl linkages and from 1 to about 12 carbon atoms or from 1 to about 6 carbon atoms; alkylsulfonyl groups including those moieties having one or more (e.g., 1, 2, 3 or 4) sulfonyl linkages and from 1 to about 12 carbon atoms or from 1 to about 6 carbon atoms; aminoalkyl groups such as groups having one or more (e.g., 1, 2, 3 or 4) N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

Any compound that is a prodrug of a compound of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I), or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

As used herein, the terms "treat", "treating" and "treatment" include the eradication, removal, reversion, alleviation, modification, or control of a sigma receptor mediated disease or condition.

As used herein, the terms "prevention", "preventing", "preventive", "prevent" and prophylaxis refer to the capacity of a compound of formula (I) to avoid, minimize or difficult the onset or development of a sigma receptor mediated disease or condition before its onset.

The term "pharmacological tool" refers to the property of compounds of the invention through which they are particularly selective ligands for Sigma receptors which implies that compound of formula (I), described in this invention, can be used as a model for testing other compounds as sigma ligands, ex. a radiactive ligands being replaced, and can also be used for modeling physiological actions related to sigma receptors.

In one embodiment, $R^1$ in formula (I) above is selected from a 5- to 10 membered substituted or unsubstituted, aromatic or non-aromatic heterocyclyl group which preferably contains N, O or S as ring member; a 5- to 10 membered substituted or unsubstituted aryl group; and a 5- to 10 membered substituted or unsubstituted cycloalkyl group.

In a preferred embodiment, $R^1$ in formula (I) above is selected from substituted or unsubstituted cyclopentyl, substituted or unsubstituted cyclohexyl, substituted or unsubstituted phenyl, substituted or unsubstituted naphtyl, substituted or unsubstituted thiophene, substituted or unsubstituted benzothiophene, substituted or unsubstituted benzofuran, substituted or unsubstituted pyridine and substituted or unsubstituted quinoline.

In a still more preferred embodiment, $R^1$ in formula (I) above is selected from the group consisting of: 2-thienyl, 3-thienyl, 2,5-dichloro-3-thienyl, 2,3-dichloro-5-thienyl, 2,3-dichloro-4-thienyl, 2-benzothienyl, 3-benzothienyl, 4-benzothienyl, 5-benzothienyl, 7-benzothienyl, 2-benzofuryl, 5-benzofuryl, 2-pyridyl, 3-pyridyl, 4-pyridyl, 2-quinolyl, 3-quinolyl, 5-quinolyl, 6-quinolyl, 3,4-difluorophenyl, 3,4-dichlorophenyl, cyclopentyl and cyclohexyl.

In another preferred embodiment, $R^1$ in formula (I) above is an α or β naphthyl, preferably selected from the following α or β naphthyl groups: 7-hydroxy-2-naphtyl, 6-hydroxy-2-naphtyl, 5-hydroxy-2-naphtyl, 6-fluoro-2-naphtyl, 6-methoxy-2-naphtyl, 6-bromo-2-naphtyl, 6-hydroxymethyl-2-naphtyl, 6-fluoromethyl-2-naphtyl, 7-hydroxy-1-naphtyl, 6-hydroxy-1-naphtyl, 5-hydroxy-1-naphtyl, 5-fluoro-1-naphtyl, 5-bromo-1-naphtyl and 1-naphtyl.

In another embodiment, $R^2$ and $R^3$ in formula (I) are independently selected from H and substituted or unsubstituted $C_{1-6}$ alkyl group, preferably methyl. More particular embodiments are those wherein $R^2$ is methyl and $R^3$ is H, or $R^2$ and $R^3$ are simultaneously H, or simultaneously methyl.

In a preferred embodiment, $R^4$ and $R^5$ form together with the nitrogen atom to which they are attached a substituted or unsubstituted heterocyclyl group. More preferably, $R^4$ and $R^5$ form together a morpholine-4-yl group, a piperidine group, pyrrolidine group or a piperazine-4-yl group.

Preferred values for m and n are independently 1 and 2.

Further, X preferably represents an oxygen atom or a —$CH_2$— group.

In additional preferred embodiments, the preferences described above for the different substituents are combined. The present invention is also directed to such combinations of preferred substitutions in the formula (I) above.

Particular individual compounds of the invention falling under formula (I) include the compounds listed below:

4-(2-((1-(3,4-dichlorophenyl)-5-methyl-1H-pyrazol-3-yl)methoxy)ethyl)morpholine,
4-(2-((5-methyl-1-(naphthalen-2-yl)-1H-pyrazol-3-yl)methoxy)ethyl)morpholine,
4-(3-(1-(3,4-dichlorophenyl)-5-methyl-1H-pyrazol-3-yl)propyl)morpholine,
4-(3-(5-methyl-1-(naphthalen-2-yl)-1H-pyrazol-3-yl)propyl)morpholine,
4-(2-(2-(1-(3,4-dichlorophenyl)-5-methyl-1H-pyrazol-3-yl)ethoxy)ethyl)morpholine,
4-(2-((1-cyclohexyl-5-methyl-1H-pyrazol-3-yl)methoxy)ethyl)morpholine,
4-(3-(1-cyclohexyl-5-methyl-1H-pyrazol-3-yl)propyl)morpholine,
1-(3,4-dichlorophenyl)-5-methyl-3-((2-(pyrrolidin-1-yl)ethoxy)methyl)-1H-pyrazole,
1-(2-((1-(3,4-dichlorophenyl)-5-methyl-1H-pyrazol-3-yl)methoxy)ethyl)piperidine,
1-(4-(2-((1-(3,4-dichlorophenyl)-5-methyl-1H-pyrazol-3-yl)methoxy)ethyl)piperazin-1-yl)ethanone,
(2S,6R)-4-(2-((1-(3,4-dichlorophenyl)-5-methyl-1H-pyrazol-3-yl)methoxy)ethyl)-2,6-dimethylmorpholine,
4-(2-((5-methyl-1-(quinolin-3-yl)-1H-pyrazol-3-yl)methoxy)ethyl)morpholine,
4-(4-(1-(3,4-dichlorophenyl)-5-methyl-1H-pyrazol-3-yl)butyl)morpholine,
4-(3-(5-methyl-1-(quinolin-3-yl)-1H-pyrazol-3-yl)propyl)morpholine,
4-(2-((1-(3,4-dichlorophenyl)-1H-pyrazol-3-yl)methoxy)ethyl)morpholine,
4-(2-((1-(3,4-dichlorophenyl)-4,5-dimethyl-1H-pyrazol-3-yl)methoxy)ethyl)morpholine,
4-(3-(1-(quinolin-3-yl)-1H-pyrazol-3-yl)propyl)morpholine,
4-(4-(1-(3,4-dichlorophenyl)-1H-pyrazol-3-yl)butyl)morpholine,
4-(4-(5-methyl-1-(quinolin-3-yl)-1H-pyrazol-3-yl)butyl)morpholine,
4-(3-((1-cyclohexyl-5-methyl-1H-pyrazol-3-yl)methoxy)propyl)morpholine,
4-(2-((1-cyclopentyl-5-methyl-1H-pyrazol-3-yl)methoxy)ethyl)morpholine,
1-(4-(2-((1-cyclohexyl-5-methyl-1H-pyrazol-3-yl)methoxy)ethyl)piperazin-1-yl)ethanone hydrochloride,
(3S,5R)-1-(2-((1-cyclohexyl-5-methyl-1H-pyrazol-3-yl)methoxy)ethyl)-3,5-dimethylpiperazine hydrochloride,
4-(2-(2-(1-cyclohexyl-5-methyl-1H-pyrazol-3-yl)ethoxy)ethyl)morpholine hydrochloride,
4-(2-((1-cyclohexyl-1H-pyrazol-3-yl)methoxy)ethyl)morpholine hydrochloride,
4-(2-((1-cyclohexyl-4,5-dimethyl-1H-pyrazol-3-yl)methoxy)ethyl)morpholine hydrochloride,
1-(4-(2-((1-cyclohexyl-1H-pyrazol-3-yl)methoxy)ethyl)piperazin-1-yl)ethanone,
1-(4-(3-((1-cyclohexyl-1H-pyrazol-3-yl)methoxy)propyl)piperazin-1-yl)ethanone,
1-(4-(4-((1-cyclohexyl-1H-pyrazol-3-yl)methoxy)butyl)piperazin-1-yl)ethanone,
1-(4-(4-((1-cyclohexyl-5-methyl-1H-pyrazol-3-yl)methoxy)butyl)piperazin-1-yl)ethanone,
1-(4-(3-((1-cyclohexyl-5-methyl-1H-pyrazol-3-yl)methoxy)propyl)piperazin-1-yl)ethanone,
1-(4-(2-((1-(3,4-dichlorophenyl)-1H-pyrazol-3-yl)methoxy)ethyl)piperazin-1-yl)ethanone,
1-(4-(3-((1-(3,4-dichlorophenyl)-1H-pyrazol-3-yl)methoxy)propyl)piperazin-1-yl)ethanone,
1-(4-(4-((1-(3,4-dichlorophenyl)-1H-pyrazol-3-yl)methoxy)butyl)piperazin-1-yl)ethanone,
1-(4-(3-((1-(3,4-dichlorophenyl)-5-methyl-1H-pyrazol-3-yl)methoxy)propyl)piperazin-1-yl)ethanone,
1-(4-(3-((1-(3,4-difluorophenyl)-1H-pyrazol-3-yl)methoxy)propyl)piperazin-1-yl)ethanone,
1-(4-(3-((1-(3,4-difluorophenyl)-5-methyl-1H-pyrazol-3-yl)methoxy)propyl)piperazin-1-yl)ethanone,
1-(4-(2-((1-(3,4-difluorophenyl)-5-methyl-1H-pyrazol-3-yl)methoxy)ethyl)piperazin-1-yl)ethanone,
1-(4-(2-((1-(3,4-difluorophenyl)-1H-pyrazol-3-yl)methoxy)ethyl)piperazin-1-yl)ethanone,
4-(2-((1-(3,4-difluorophenyl)-5-methyl-1H-pyrazol-3-yl)methoxy)ethyl)morpholine,
4-(2-((1-(3,4-difluorophenyl)-1H-pyrazol-3-yl)methoxy)ethyl)morpholine,
4-(3-((1-(3,4-difluorophenyl)-5-methyl-1H-pyrazol-3-yl)methoxy)propyl)morpholine,
1-(4-(2-((1-cyclohexyl-5-methyl-1H-pyrazol-3-yl)methoxy)ethyl)piperazin-1-yl)propan-1-one,
1-(4-(2-((1-cyclohexyl-5-methyl-1H-pyrazol-3-yl)methoxy)ethyl)piperazin-1-yl)-2-methylpropan-1-one,
1-(4-(2-((1-cyclohexyl-1H-pyrazol-3-yl)methoxy)ethyl)piperazin-1-yl)propan-1-one,
1-(4-(2-((1-cyclohexyl-1H-pyrazol-3-yl)methoxy)ethyl)piperazin-1-yl)-2-methylpropan-1-one,
1-(4-(2-((1-(3,4-dichlorophenyl)-5-methyl-1H-pyrazol-3-yl)methoxy)ethyl)piperazin-1-yl)propan-1-one,
1-(4-(2-((1-(3,4-dichlorophenyl)-5-methyl-1H-pyrazol-3-yl)methoxy)ethyl)piperazin-1-yl)-2-methylpropan-1-one,
1-(4-(2-((1-(3,4-dichlorophenyl)-1H-pyrazol-3-yl)methoxy)ethyl)piperazin-1-yl)propan-1-one,
1-(4-(2-((1-(3,4-dichlorophenyl)-1H-pyrazol-3-yl)methoxy)ethyl)piperazin-1-yl)-2-methylpropan-1-one, or a pharmaceutically acceptable salt, prodrug or solvate thereof.

Another aspect of the present invention relates to processes for the preparation of compounds of general formula (I) as described above.

Compounds corresponding to preferred embodiments according to general formula (Ia), (Ib), (Ic) and (Id) could be prepared as follows:

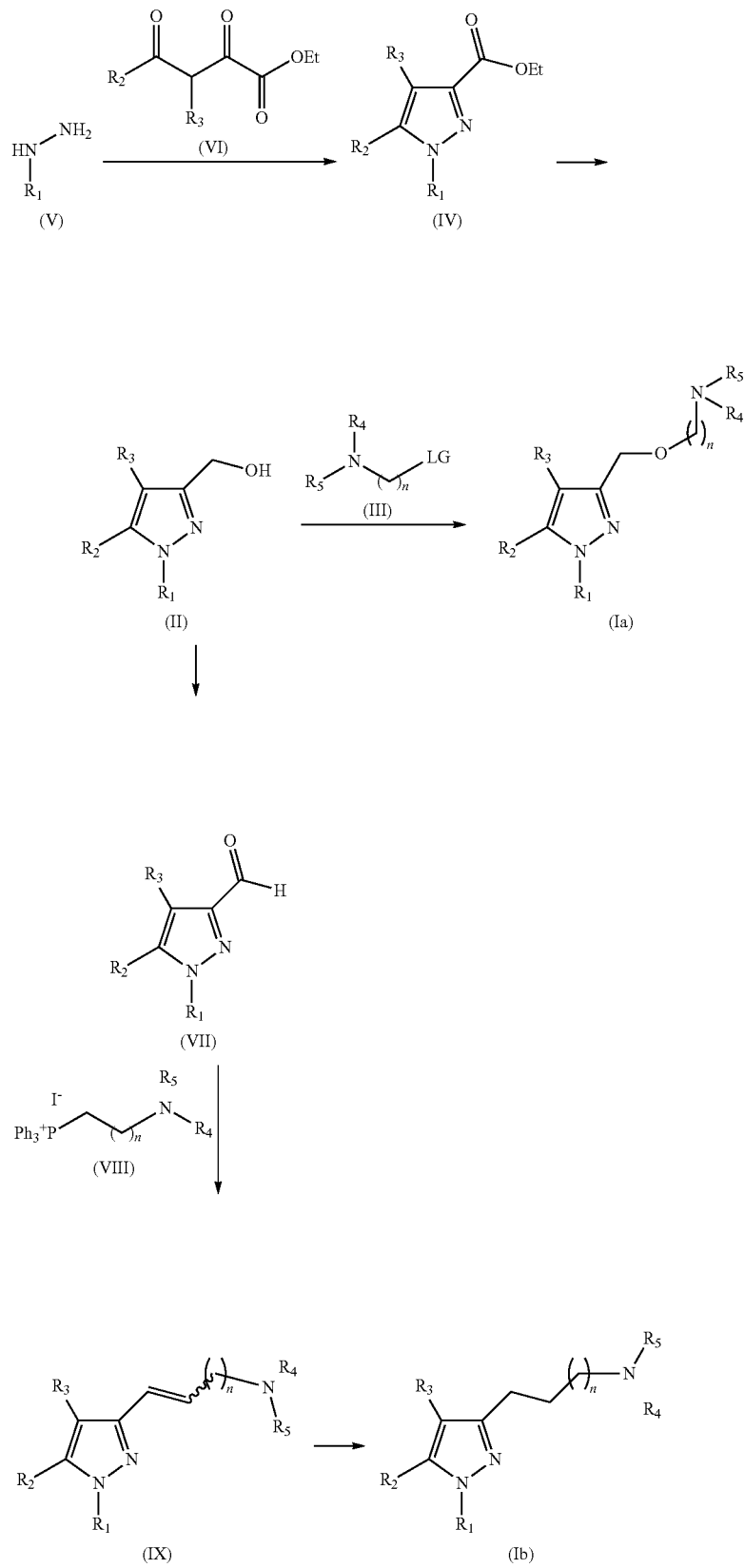

Reaction scheme (II)
Method A
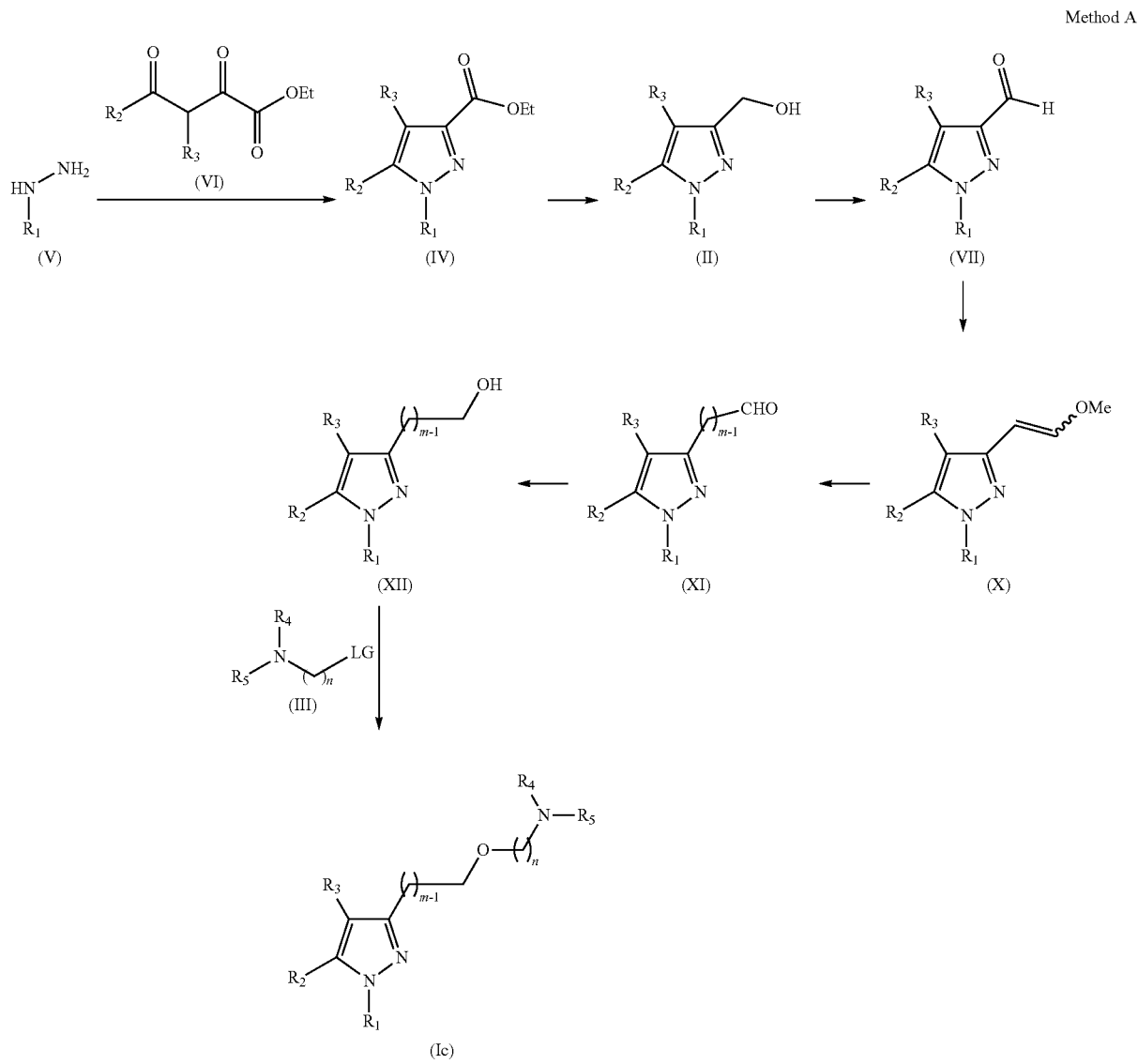
Method B
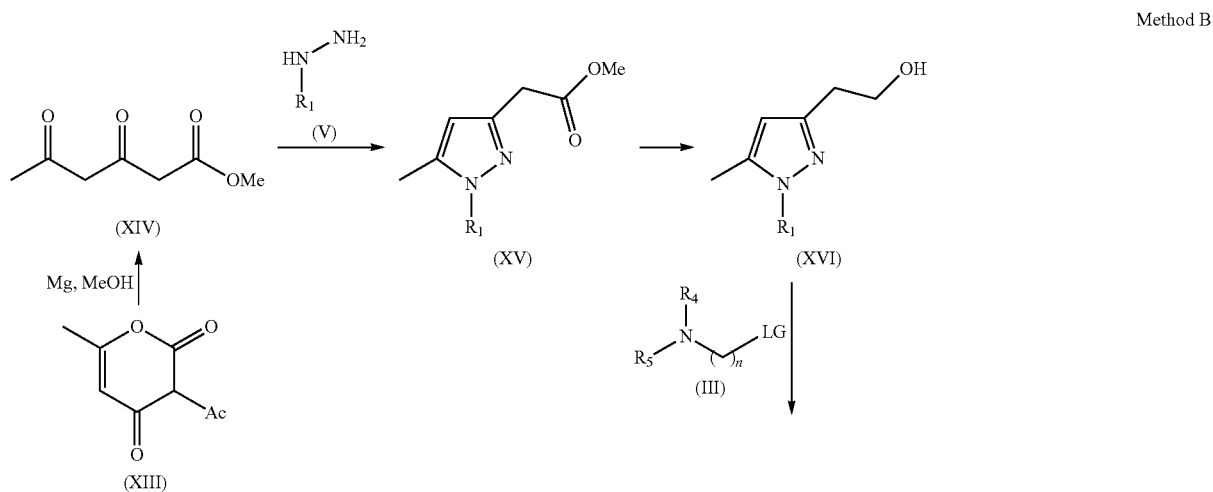

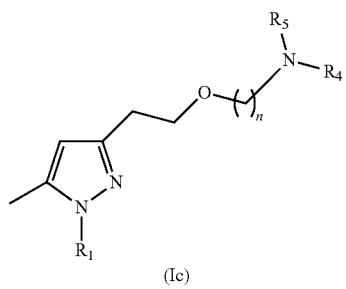

(Ic)

Reaction scheme (III)

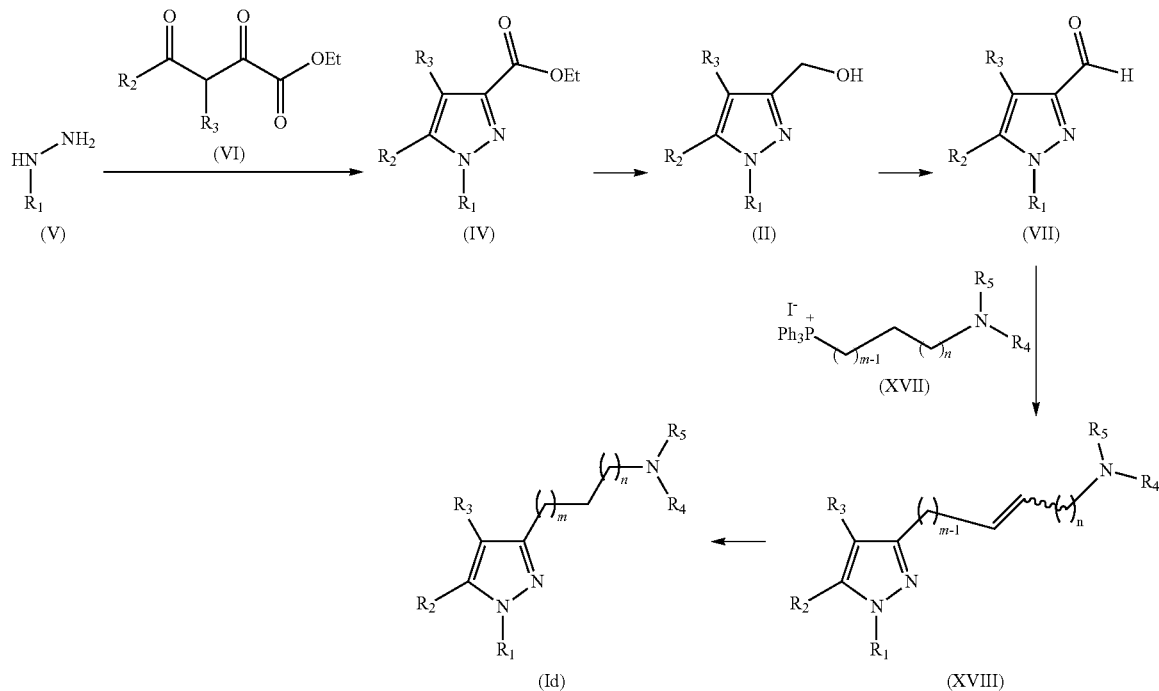

Process for Preparing a Compound of Formula (Ia):

Reaction of a compound of formula (II) with a compound of formula (III) in the presence of a base and a suitable solvent; where LG represents a leaving group that may be selected from a halide, e.g. bromide or chloride, or an arylsulfonyl group, e.g. mesylate, triflate, or tosylate, and the like. This reaction is conducted in a suitable solvent that will be a reaction-inert solvent, such as hydrocarbons like toluene; halogenated hydrocarbons, e.g. dichloromethane, chloroform; dipolar aprotic solvents such as acetonitrile, N,N-dimethylformamide (DMF), N,N-dimethylacetamide (DMA), dimethylsulfoxide (DMSO), hexamethylphosphoric triamide (HMPT); ethers such as tetrahydrofuran (THF), mixtures thereof with water, and the like. The base is strong enough to detract a hydrogen from the hydroxy group, for example an alkali of alkaline metal hydride such as lithium hydride or sodium hydride, or an alkali metal alkoxide such as sodium or potassium methoxide or ethoxide, potassium tert-butoxide, or potassium carbonate, triethylamine, pyridine, sodium iodide, cesium carbonate, etc.

Compounds of formula (III) are commercially available or obtained by methods known by the skilled in the art as for instance described in EP0529973.

Intermediates of formula (II) may be obtained as described in WO2007079086, by reduction of a compound of formula (IV).

Pyrazole carboxylates of formula (IV) may be obtained as described in WO2007079086, by reaction of a hydrazine derivative (V) with an 1,3-diketone of formula (VI) in a suitable solvent such as acetic acid.

Hydrazines (V) may be commercially available or obtained from a suitable nitro, amino or halo substituted derivative by methods generally known by the skilled in the art. (J. Am. Chem. Soc. 1998, 120, 6621; Angew. Chem., Int. Ed, 1998, 37, 2090).

1,3-diketones (VI) may be obtained by a Claisen condensation between an alkyl ketone of formula $CH_3COR_2$ and diethyl oxalate.

Process for Preparing a Compound of Formula (Ib):

Compounds of formula (Ib) may be obtained by reduction of a compound of formula (IX) by methods known by the skilled in the art (Paul N. Rylander in "Hydrogenation Methods", Ed. Academic Press, 1990).

Compound of formula (IX) may be obtained by reaction of a compound of formula (VII) with a phosphonium salt of formula (VIII) in the presence of a base and a suitable solvent. The suitable solvent will be a reaction-inert solvent, such as hydrocarbons like toluene; halogenated hydrocarbons, e.g. dichloromethane, chloroform; dipolar aprotic solvents such as N,N-dimethylformamide (DMF), and the like; ethers such as tetrahydrofuran (THF), and the like; and the base, for example an alkali of alkaline metal hydride such as or sodium hydride, or an alkali metal alkoxide such as sodium or potassium methoxide or ethoxide, potassium tert-butoxide, or potassium carbonate, butyl lithium, triethylamine, pyridine, etc. (*Chem. Rev.* 1989, 89, 863-927; *Top. Stereochem.* 1994, 21, 1).

Phosphonium salts (VIII) are obtained by methods known by the skilled in the art from commercially available halides by reaction with triphenylphospine in the presence of a suitable solvent. (I. Gosney, A. G. Rowley in "*Organophosphorous Reagents in Organic Synthesis*", Ed. J. I. G. Cadogan, Academic Press, New York, 1979, Chpt 2; *J. Org. Chem.* 1984, 49, 4293-4295 and references cited therein).

Compounds of formula (VII) may be obtained by oxidation of the above described intermediates (II) in the presence of a suitable oxidant agent such as Manganese (IV) oxide in a suitable solvent such as halogenated hydrocarbons, e.g. dichloromethane, chloroform. (Gabriel Tojo, Marcos Fernández in "*Oxidation of Alcoholes to Aldehydes and Ketones: A Guide to Current Common Practice*", Ed. Springer, 2006, Chpt 8).

Process for Preparing a Compound of Formula (Ic):
According to Method A:

Reaction of a compound of formula (XII) with a compound of formula (III) in the presence of a base and a suitable solvent; where LG represents a leaving group that may be selected from a halide, e.g. bromide or chloride, or an arylsulfonyl group, e.g. mesylate, triflate, or tosylate, and the like. This reaction is conducted in a suitable solvent that will be a reaction-inert solvent, such as hydrocarbons like toluene; halogenated hydrocarbons, e.g. dichloromethane, chloroform; dipolar aprotic solvents such as acetonitrile, N,N-dimethylformamide (DMF), N,N-dimethylacetamide (DMA), dimethylsulfoxide (DMSO), hexamethylphosphoric triamide (HMPT); ethers such as tetrahydrofuran (THF), mixtures thereof with water, and the like. The base is strong enough to detract a hydrogen from the hydroxy group, for example an alkali of alkaline metal hydride such as lithium hydride or sodium hydride, or an alkali metal alkoxide such as sodium or potassium methoxide or ethoxide, potassium tert-butoxide, or potassium carbonate, triethylamine, pyridine, sodium iodide, cesium carbonate, etc.

Compounds of formula (III) are commercially available or obtained by methods known by the skilled in the art as for instance described in EP0529973.

Intermediates of formula (XII) may be obtained as described in WO2007079086, by reduction of a compound of formula (XI).

Compounds of formula (XI) may be obtained by acid hydrolysis by methods known by the skilled in the art.

Compound of formula (X) may be obtained by reaction of a compound of formula (VII) with a phosphonium salt in the presence of a base and a suitable solvent. The suitable solvent will be a reaction-inert solvent, such as hydrocarbons like toluene; halogenated hydrocarbons, e.g. dichloromethane, chloroform; dipolar aprotic solvents such as N,N-dimethylformamide (DMF), and the like; ethers such as tetrahydrofuran (THF), and the like; and the base, for example an alkali of alkaline metal hydride such as or sodium hydride, or an alkali metal alkoxide such as sodium or potassium methoxide or ethoxide, potassium tert-butoxide, or potassium carbonate, butyl lithium, triethylamine, pyridine, etc. (*Chem. Rev.* 1989, 89, 863-927; *Top. Stereochem.* 1994, 21, 1).

Phosphonium salts are obtained by methods known by the skilled in the art from commercially available halides by reaction with triphenylphospine in the presence of a suitable solvent. (I. Gosney, A. G. Rowley in "*Organophosphorous Reagents in Organic Synthesis*", Ed. J. I. G. Cadogan, Academic Press, New York, 1979, Chpt 2; *J. Org. Chem.* 1984, 49, 4293-4295 and references cited therein).

Compounds of formula (VII) may be obtained by oxidation of the above described intermediates (II) in the presence of a suitable oxidant agent such as manganese oxide in a suitable solvent such as halogenated hydrocarbons, e.g. dichloromethane, chloroform. (Gabriel Tojo, Marcos Fernández in "*Oxidation of Alcoholes to Aldehydes and Ketones: A Guide to Current Common Practice*", Ed. Springer, 2006, Chpt 8).

Intermediates of formula (II) may be obtained as described in WO2007079086, by reduction of a compound of formula (IV).

Pyrazole carboxylates of formula (IV) may be obtained as described in WO2007079086, by reaction of a hydrazine derivative (V) with an 1,3-diketone of formula (VI) in a suitable solvent such as acetic acid.

Hydrazines (V) may be commercially available or obtained from a suitable nitro, amino or halo substituted derivative by methods generally known by the skilled in the art. (*J. Am. Chem. Soc.* 1998, 120, 6621; *Angew. Chem., Int. Ed.* 1998, 37, 2090).

1,3-diketones (VI) may be obtained by a Claisen condensation between an alkyl ketone of formula $CH_3COR_2$ and diethyl oxalate.

According to Method B:

Reaction of a compound of formula (XVI) with a compound of formula (III) in the presence of a base and a suitable solvent; where LG represents a leaving group that may be selected from a halide, e.g. bromide or chloride, or an arylsulfonyl group, e.g. mesylate, triflate, or tosylate, and the like. This reaction is conducted in a suitable solvent that will be a reaction-inert solvent, such as hydrocarbons like toluene; halogenated hydrocarbons, e.g. dichloromethane, chloroform; dipolar aprotic solvents such as acetonitrile, N,N-dimethylformamide (DMF), N,N-dimethylacetamide (DMA), dimethylsulfoxide (DMSO), hexamethylphosphoric triamide (HMPT); ethers such as tetrahydrofuran (THF), mixtures thereof with water, and the like. The base is strong enough to detract a hydrogen from the hydroxy group, for example an alkali of alkaline metal hydride such as lithium hydride or sodium hydride, or an alkali metal alkoxide such as sodium or potassium methoxide or ethoxide, potassium tert-butoxide, or potassium carbonate, triethylamine, pyridine, sodium iodide, cesium carbonate, etc.

Compounds of formula (III) are commercially available or obtained by methods known by the skilled in the art as for instance described in EP0529973.

Intermediates of formula (XVI) may be obtained as described in WO2007079086, by reduction of a compound of formula (XV), Pyrazole carboxylates of formula (XV) may be obtained as described in WO2007079086, by reaction of a hydrazine derivative (V) with methyl 3,5-dioxohexanoate of formula (XIV) in a suitable solvent such as MeOH.

Hydrazines (V) may be commercially available or obtained from a suitable nitro, amino or halo substituted derivative by methods generally known by the skilled in the art. (*J. Am. Chem. Soc.* 1998, 120, 6621; *Angew. Chem., Int. Ed.* 1998, 37, 2090).

Methyl 3,5-dioxohexanoate of formula (XIV) may be obtained by reaction of an commercially available dehydroacetic acid (XIII) with magnesium in MeOH (*Tetrahedron Letters* 2010, 51, 2741).

Process for Preparing a Compound of Formula (Id):

The procedure is the same as described above for compounds of formula (Ib), using the appropriate compound (XVII).

During the processes described above the protection of sensitive groups or of reagents may be necessary and/or desirable. The introduction of conventional protective groups as well as their removal may be performed by methods well-known to those skilled in the art.

If the compounds of general formula (I) themselves are obtained in form of a mixture of stereoisomers, particularly enantiomers or diastereomers, said mixtures may be separated by standard procedures known to those skilled in the art, e.g. chromatographic methods or fractionalized crystallization with chiral reagents. If there are chiral centers the compounds may be prepared in racemic form, or individual enantiomers may be prepared either by enantiospecific synthesis or by resolution.

Solvates, preferably hydrates, of the compounds of general formula (I), of corresponding stereoisomers, or of corresponding salts thereof may also be obtained by standard procedures known to those skilled in the art.

The purification and isolation of the inventive compounds of general formula (I), of a corresponding stereoisomer, or salt, or solvate or any intermediate thereof may, if required, be carried out by conventional methods known to those skilled in the art, e.g. chromatographic methods or recrystallization.

It has been found that the compounds of general formula (I), stereoisomers thereof, corresponding salts and corresponding solvates have high affinity to sigma receptors, i.e. they are selective ligands for the sigma receptor and act as modulators, e.g. antagonists, inverse agonists or agonists, on these receptors.

The present invention further provides medicaments or pharmaceutical compositions comprising a compound of this invention, or a pharmaceutically acceptable salt, derivative, prodrug or stereoisomers thereof together with a pharmaceutically acceptable excipient, for administration to a patient, notably a human.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker,© 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E.W. Marlin. The selection of these excipients and the amounts to be used will depend on the form of application of the pharmaceutical composition.

The medicament or pharmaceutical composition according to the present invention may be in any form suitable for the application to humans and/or animals, preferably humans including infants, children and adults and can be produced by standard procedures known to those skilled in the art. Therefore, the formulation in accordance with the invention may be adapted for topical or systemic application, particularly for dermal, transdermal, subcutaneous, intramuscular, intra-articular, intraperitoneal, intravenous, intra-arterial, intravesical, intraosseous, intracavernosal, pulmonary, buccal, sublingual, ocular, intravitreal, intranasal, percutaneous, rectal, vaginal, oral, epidural, intrathecal, intraventricular, intracerebral, intracerebroventricular, intracisternal, intraspinal, perispinal, intracranial, delivery via needles or catheters with or without pump devices, or other application routes.

In a preferred embodiment the pharmaceutical compositions are in oral form, either solid or liquid. Suitable dose forms for oral administration may be tablets, pills, caplets, gel caps, chewing gums, capsules, granules, drops, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or reconstitutable dry preparations, aerosols or sprays in the appropriate unit dosage form. Adequate excipients can be used, such as bulking agents, buffering agents or surfactants.

The composition of the invention may be formulated as deposits in dissolved form or in patches, for percutaneous application.

Skin applications include ointments, gels, creams, lotions, suspensions or emulsions. Suitable form of rectal application is by means of suppositories.

The mentioned formulations will be prepared using standard methods such as those described or referred to in the Spanish and US Pharmacopoeias and similar reference texts.

In one embodiment of the invention it is preferred that compound of formula (I) is used in therapeutically effective amounts. The physician will determine the dosage of the present therapeutic agents which will be most suitable and it will vary with the form of administration and the particular compound chosen, and furthermore, it will vary with the patient under treatment, the age of the patient, the type of disease or condition being treated. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. Active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are merely illustrative of certain embodiments of the invention and cannot be considered as restricting it in any way.

EXAMPLES

Example 1

Synthesis of 4-(2-{[1-(3,4-dichlorophenyl)-5-methyl-1H-pyrazol-3-yl]methoxy}ethyl)morpholine

1.1 Synthesis of ethyl 1-(3,4-dichlorophenyl)-5-methyl-1H-pyrazole-3-carboxylate

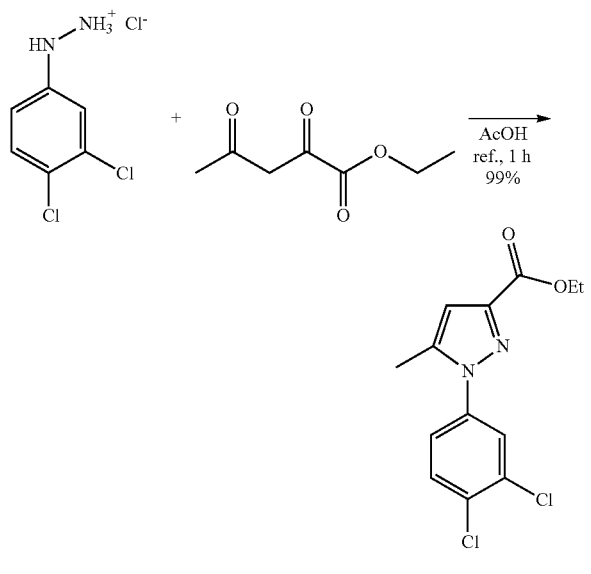

Ethyl acetopyruvate (74 mg, 0.468 mmol) was added over a suspension of the starting material (100 mg, 0.468 mmol) in AcOH (5 mL) and the mixture was refluxed for 1 h. Then, it was allowed to cool to rt and diluyed with $CH_2Cl_2$ (10 mL). The organic phase was washed with $H_2O$ (1×10 mL) and with NaOH ac. 10% (2×10 mL), dried over $Na_2SO_4$ anh., filtered and concentrated to dryness. The residue (171 mg) was purified by flash column chromatography in silica gel (21% AcOEt/hexane), to yield 139 mg of the desired product (Rf=0.6 (30% AcOEt/hexane), pale yellow solid, 99% yield).

NMR-$^1$H (CDCl$_3$, 250 MHz, δ): 7.62 (d, J=2.4 Hz, 1H, ArH); 7.54 (d, J=8.3 Hz, 1H, ArH); 7.32 (dd, J=2.4 and 8.3 Hz, 1H, ArH); 6.72 (s, 1H, ArH); 4.39 (c, J=6.8 Hz, 2H, CH$_2$); 2.34 (s, 3H, CH$_3$); 1.39 (t, J=6.8 Hz, 3H, CH$_3$).

MS-EI+m/z: 300.0 (M+1).

1.2 Synthesis of [1-(3,4-dichlorophenyl)-5-methyl-1H-pyrazol-3-yl]methanol

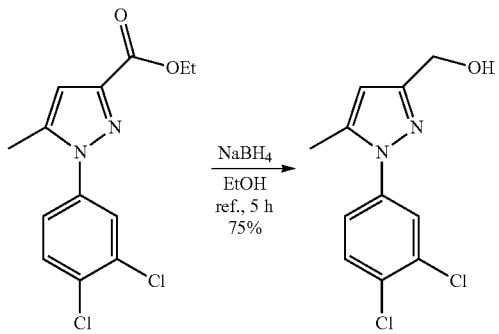 [SMILES: CCOC(=O)c1cc(C)n(-c2ccc(Cl)c(Cl)c2)n1 ; "NaBH4" ; Cc1cc(CO)nn1-c1ccc(Cl)c(Cl)c1]

NaBH$_4$ (104 mg, 2.76 mmol) was added over a suspension of the starting ester (551 mg, 1.84 mmol) in EtOH (12 mL). The mixture was refluxed (it is dissolved when refluxing) for 1 h, and more NaBH$_4$ was added (104 mg, 2.76 mmol) then. It was refluxed for further 4 h, and it was allowed to cool to rt. It was poured into H$_2$O (10 mL), and the aqueous layer was extracted with CH$_2$Cl$_2$ (2×10 mL). The combined organic phases were washed with NH$_4$Cl ac. sat. (1×15 mL) and with H$_2$O (1×15 mL), dried over Na$_2$SO$_4$ anh., filtered and concentrated to dryness. The residue was purified by flash column chromatography in silica gel (42-60% AcOEt/hexane) to yield 354 mg of the desired product (Rf=0.5 (10% MeOH/CH$_2$Cl$_2$), yellow solid, 75% yield).

NMR-$^1$H (CDCl$_3$, 250 MHz, δ): 7.82 (d, J=2.5 Hz, 1H, ArH); 7.75 (d, J=8.5 Hz, 1H, ArH): 7.52 (m, 1H, ArH); 6.43 (s, 1H, ArH); 4.91 (s, 2H, CH$_2$); 2.57 (s, 3H, CH$_3$).

1.3 Synthesis of 4-(2-iodoethyl)morpholine

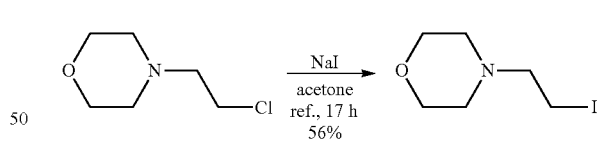

NaI (25.54 g, 170.40 mmol) was added over a suspension of the starting chloride (8.5 g, 56.80 mmol) in acetone (150 mL). The mixture was refluxed for 17 h, then it was allowed to cool to rt and filtered, washing with CH$_2$Cl$_2$ (3×100 mL). The filtrate was washed with H$_2$O (3×250 mL), the organic phase was dried over Na$_2$SO$_4$ anh., filtered and concentrated to dryness to yield 7.71 g of the desired iodide (Rf=0.4 (40% AcOEt/hexane), oily yellow solid, 56% yield).

NMR-$^1$H (CDCl$_3$, 250 MHz, δ): 3.64 (t, J=4.7 Hz, 4H, CH$_2$); 3.14 (t, J=7.6 Hz, 2H, CH$_2$) 2.65 (t, J=7.6 Hz, 2H, CH$_2$) 2.42 (t, J=4.7 Hz, 4H, CH$_2$).

1.4 Synthesis of 4-(2-{[1-(3,4-dichlorophenyl)-5-methyl-1H-pyrazol-3-yl]methoxy}ethyl)morpholine

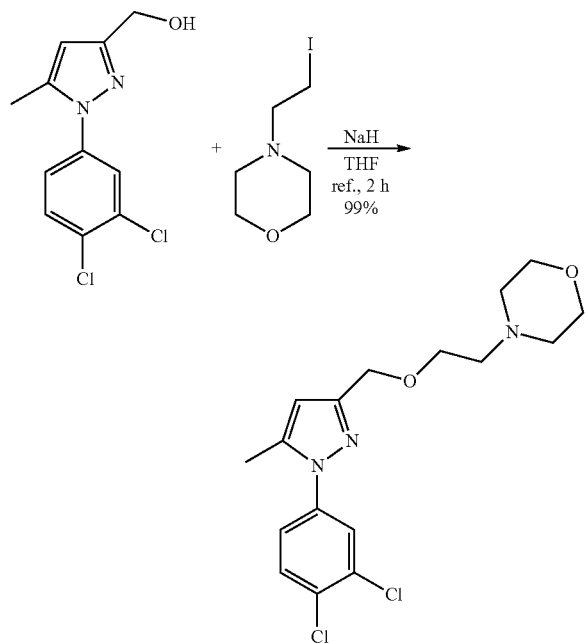

NaH (60% in mineral oil, 25 mg, 0.622 mmol) was added over a solution of the starting alcohol (80 mg, 0.311 mmol) in THF (3 mL). The mixture was stirred at rt for 10 min h, and the starting iodide was added (225 mg, 0.933 mmol) in THF (2 mL). The mixture was refluxed for 2 h, then it was allowed to cool to rt and it was poured into NaHCO$_3$ ac. sat. (8.0 mL). CH$_2$Cl$_2$ (10 mL) was added and the organic phase was separated. The aqueous phase was extracted with CH$_2$Cl$_2$ (2×8 mL), and the combined organic phases were dried over Na$_2$SO$_4$ anh., filtered and concentrated to dryness. The residue was purified by flash column chromatography in silica gel (3-5.2% MeOH/CH$_2$Cl$_2$) to yield 114 mg of the desired product (Rf=0.5 (10% MeOH/CH$_2$Cl$_2$), cream solid, 99% yield).

NMR-$^1$H (CDCl$_3$, 250 MHz, δ): 7.59 (d, J=2.5 Hz, 1H, ArH); 7.52 (d, J=8.6 Hz, 1H, ArH); 7.32-7.27 (dd, J=2.5 and 8.6 Hz, 1H, ArH); 6.24 (s, 1H, ArH); 4.54 (s, 2H, CH$_2$); 3.73 (t, J=4.6 Hz, 4H, CH$_2$); 3.65 (t, J=5.8 Hz, 2H, CH$_2$); 2.62 (t, J=5.8 Hz, 2H, CH$_2$); 2.51 (t, J=4.6 Hz, 4H, CH$_2$); 2.35 (s, 3H, CH$_3$).

MS-EI+m/z: 370.3, 372.3 (M+1).

Example 2

Synthesis of 4-(2-{[1-(2-naphthyl)-5-methyl-1H-pyrazol-3-yl]methoxy}ethyl)morpholine

2.1 Synthesis of 2-naphthylhydrazine hydrochloride

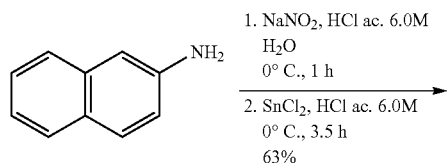

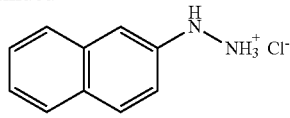

NaNO$_2$ (578 mg, 8.38 mmol) in H$_2$O (1.2 mL) was slowly added (2 min of addition) over a suspension of 2-naphthylamine (800 mg, 5.59 mmol) in HCl ac. 6.0 M (6 mL) cooled in a H$_2$O-ice bath. The resulting solution was stirred in H$_2$O-ice bath for 1 h, and SnCl$_2$ (3.71 g, 19.56 mol) was added slowly (5 min of addition). The resulting suspension was stirred in H$_2$O-ice bath for 3.5 h, and then filtered. The solid was successively washed with H$_2$O at 0° C. (4×8 mL), with H$_2$O at rt (1×8 mL), with Et$_2$O at 0° C. (2×4 mL), with Et$_2$O/hexane (1:1, 2×4 mL) and with hexane (2×5 mL). The solid was dried to yield 690 mg of the desired product (Rf=0.7 (40% AcOEt/hexane), cream solid, 63% yield).

NMR-$^1$H (DMSO-d$_6$, 250 MHz, δ): 7.81 (m, 2H, ArH); 7.71 (d, J=7.7 Hz, 1H, ArH); 7.49-7.19 (m, 4H, ArH).

MS-EI+m/z: 159.1 (M−HCl+1).

2.2 Synthesis of ethyl 5-methyl-1-(2-naphthyl)-1H-pyrazole-3-carboxylate

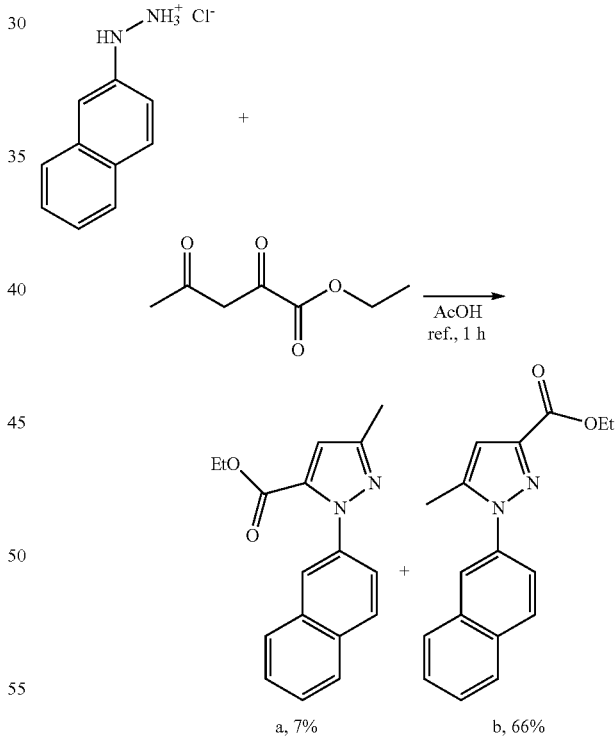

a, 7%    b, 66%

Ethyl acetopyruvate (544 mg, 3.44 mmol) was added over a suspension of the starting hydrazine (670 mg, 3.44 mmol) in AcOH (5 mL). The resulting suspension was refluxed for 1 h, then it was allowed to cool to r.t. and diluted with CH$_2$Cl$_2$ (15 mL). The organic phase was successively washed with H$_2$O (2×20 mL), with NaOH ac. 10% (1×20 mL) and again with H$_2$O (1×20 mL). The organic phase was dried over Na$_2$SO$_4$ anh., filtered and concentrated to dryness. The residue was purified by flash column chromatography in silica gel (15-

41% AcOEt/hexane), to yield 68 mg of isomer a (Rf=0.8 (20% AcOEt/hexane), orange solid, 7% yield) and 640 mg of isomer b (Rf=0.6 (20% AcOEt/hexane), organge solid, 66% yield)

NMR-$^1$H isomer b (CDCl$_3$, 250 MHz, δ): 7.95-7.84 (m, 4H, ArH); 7.60-7.51 (m, 3H, ArH); 6.78 (s, 1H, ArH); 4.43 (c, J=7.1 Hz, 2H, CH$_2$); 2.38 (s, 3H, CH$_3$); 1.40 (t, J=7.1 Hz, 3H, CH$_3$).

NMR-$^1$H isomer a (CDCl$_3$, 250 MHz, δ): 7.91-7.85 (m, 4H, ArH); 7.53-7.48 (m, 3H, ArH); 6.86 (s, 1H, ArH); 4.22 (c, J=7.1 Hz, 2H, CH$_2$); 2.39 (s, 3H, CH$_3$); 1.20 (t, J=7.1 Hz, 3H, CH$_3$).

2.3 Synthesis of [5-methyl-1-(2-naphthyl)-1H-pyrazol-3-yl]methanol

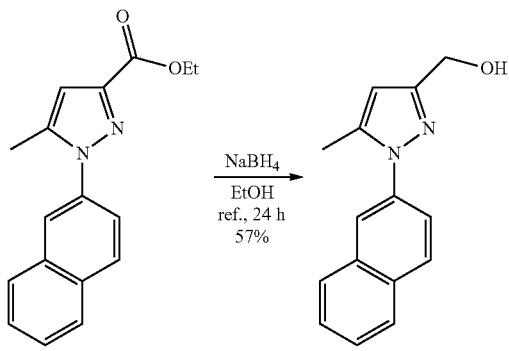 [SMILES: CCOC(=O)c1cc(C)n(-c2ccc3ccccc3c2)n1 ; "NaBH4" ; Cc1cc(CO)nn1-c1ccc2ccccc2c1]

NaBH$_4$ (129 mg, 3.42 mmol) was added over a suspension of the starting ester (640 mg, 2.28 mmol) in EtOH (15 mL). The mixture was refluxed (it is dissolved when refluxing) for 1.5 h, and then more NaBH$_4$ (640 mg, 2.28 mmol) was added. It was refluxed for another 4 h, and more NaBH$_4$ (640 mg, 2.28 mmol) was added. After another 2.5 h, more NaBH$_4$ (640 mg, 2.28 mmol) was added and it was refluxed for another 16 h, The reaction mixture was allowed to cool to rt and poured into H$_2$O (10 mL). The aqueous phase was extracted with CH$_2$Cl$_2$ (2×15 mL) and the combined organic phases were washed with NH$_4$Cl ac. sat. (2×30 mL), dried over Na$_2$SO$_4$ anh., filtered and concentrated to dryness. The residue was purified by flash column chromatography in silica gel (60-70% AcOEt/hexane), to yield 309 mg of the desired product (Rf=0.2 (40% AcOEt/hexane), yellow solid, 57% yield).

NMR-$^1$H (CDCl$_3$, 250 MHz, δ): 7.96-7.96 (m, 4H, ArH); 7.61 (d, J=1.9 Hz, 1H, ArH); 7.56 (m, 2H, ArH); 6.25 (s, 1H, ArH); 4.74 (sa, 2H, CH$_2$); 2.39 (s, 3H, CH$_3$).

2.4 Synthesis of 4-(2-{[1-(2-naphthyl)-5-methyl-1H-pyrazol-3-yl]methoxy}ethyl)morpholine

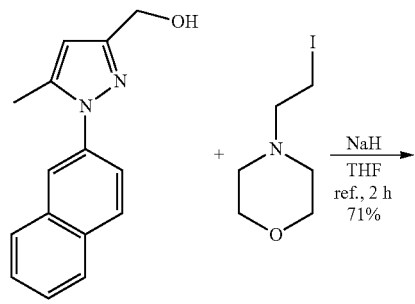

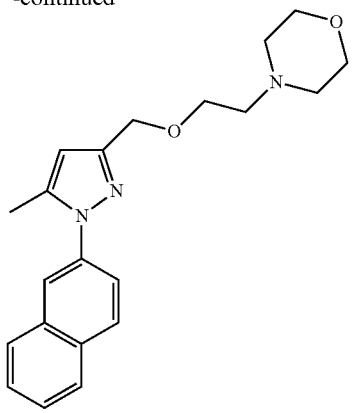

NaH (60% in mineral oil, 56 mg, 1.40 mmol) was added over a solution of the starting alcohol (167 mg, 0.70 mmol) in THF (6 mL). The mixture was stirred at it for 5 min, and the starting iodide was added (354 mg, 1.47 mmol) in THF (2 mL). The reaction mixture was refluxed for 2 h, then it was allowed to cool to r.t. and poured into NaHCO$_3$ ac. sat. mL), The aqueous phase was extracted with CH$_2$Cl$_2$ (2×10 mL) and the combined organic phases were washed with NaHCO$_3$ ac. sat. (1×20 mL) and with H$_2$O (1×10 mL), dried over Na$_2$SO$_4$ anh., filtered and concentrated to dryness. The residue was purified by flash column chromatography in silica gel (4% MeOH/CH$_2$Cl$_2$), to yield 176 mg of the desired product (Rf=0.1 (5% MeOH/CH$_2$Cl$_2$), orange oil, 71% yield).

NMR-$^1$H (CDCl$_3$, 250 MHz, δ): 7.89 (m, 4H, ArH); 7.61-7.50 (m, 3H, ArH); 6.28 (s, 1H, ArH); 4.60 (s, 2H, CH$_2$); 3.74 (t, J=4.7 Hz, 4H, CH$_2$); 3.69 (t, J=5.8 Hz, 2H, CH$_2$); 2.65 (t, J=5.8 Hz, 2H, CH$_2$); 2.53 (m, 4H, CH$_2$); 2.39 (s, 3H, CH$_3$).
MS-EI+m/z: 352.4 (M+1).

Example 3

Synthesis of 4-{3-[1-(3,4-dichlorophenyl)-5-methyl-1H-pyrazol-3-yl]propyl}morpholine

3.1 Synthesis of ethyl 1-(3,4-dichlorophenyl)-5-methyl-1H-pyrazole-3-carboxylate

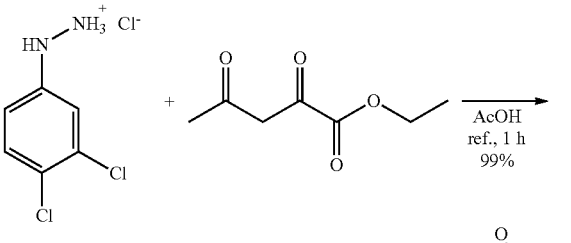

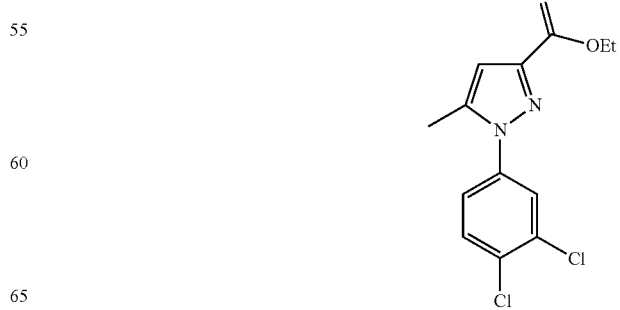

Ethyl acetopyruvate (74 mg, 0.468 mmol) was added over a suspension of the starting material (100 mg, 0.468 mmol) in AcOH (5 mL). The resulting mixture was refluxed for 1 h, then it was allowed to cool to rt and diluted with $CH_2Cl_2$ (10 mL). The organic phase was washed with $H_2O$ (1×10 mL) and with NaOH ac. 10% (2×10 mL), dried over $Na_2SO_4$ anh., filtered and concentrated to dryness. The residue (171 mg) was purified by flash column chromatography in silica gel (21% AcOEt/hexane), to yield 139 mg of the desired product (Rf=0.6 (30% AcOEt/hexane), pale yellow solid, 99% yield).

NMR-$^1$H (CDCl$_3$, 250 MHz, δ): 7.62 (d, J=2.4 Hz, 1H, ArH); 7.54 (d, J=8.3 Hz, 1H, ArH); 7.32 (dd, J=2.4 and 8.3 Hz, 1H, ArH); 6.72 (s, 1H, ArH); 4.39 (c, J=6.8 Hz, 2H, CH$_2$); 2.34 (s, 3H, CH$_3$); 1.39 (t, J=6.8 Hz, 3H, CH$_3$).

MS-EI+m/z: 300.0 (M+1).

3.2 Synthesis of [1-(3,4-dichlorophenyl)-5-methyl-1H-pyrazol-3-yl]methanol

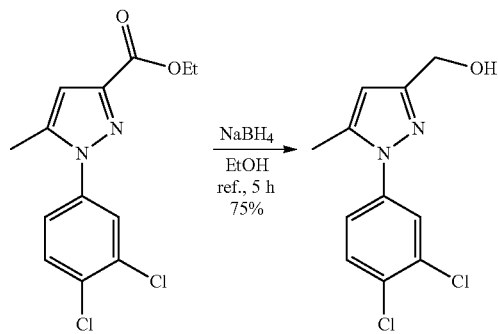 [SMILES: CCOC(=O)c1cc(C)n(-c2ccc(Cl)c(Cl)c2)n1 ; "NaBH4" ; Cc1cc(CO)nn1-c1ccc(Cl)c(Cl)c1]

NaBH$_4$ (104 mg, 2.76 mmol) was added over a suspension of the starting ester (551 mg, 1.84 mmol) in EtOH (12 mL). The mxiture was refluxed (it is dissolved when refluxing) for 1 h, and then more NaBH$_4$ (104 mg, 2.76 mmol) was added. It was refluxed for another 4 h, and then it was allowed to cool to rt and poured into $H_2O$ (10 mL), The aqueous phase was extracted with $CH_2Cl_2$ (2×10 mL) and the combined organic phases were washed with NH$_4$Cl ac. sat. (1×15 mL) and with $H_2O$ (1×15 mL), dried over $Na_2SO_4$ anh., filtered and concentrated to dryness. The residue was purified by flash column chromatography in silica gel (42-60% AcOEt/hexane), to yield 354 mg of the desired product (Rf=0.5 (10% MeOH/CH$_2$Cl$_2$), yellow solid, 75% yield).

NMR-$^1$H (CDCl$_3$, 250 MHz, δ): 7.82 (d, J=2.5 Hz, 1H, ArH); 7.75 (d, J=8.5 Hz, 1H, ArH); 7.52 (m, 1H, ArH); 6.43 (s, 1H, ArH); 4.91 (s, 2H, CH$_2$); 2.57 (s, 3H, CH$_3$).

3.3 Synthesis of 1-(3,4-dichlorophenyl)-5-methyl-1H-pyrazole-3-carbaldehyde

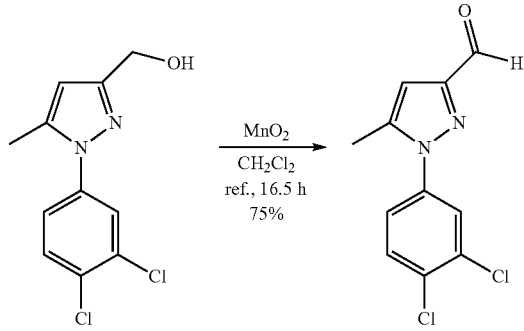 [SMILES: Cc1cc(CO)nn1-c1ccc(Cl)c(Cl)c1 ; "MnO2" ; Cc1cc(C=O)nn1-c1ccc(Cl)c(Cl)c1]

MnO$_2$ (85% purity, 2.16 g, 21.10 mmol) was added over a solution of the starting alcohol (542 mg, 2.11 mmol) in $CH_2Cl_2$ (30 mL). The mixture was refluxed for 16.5 h, and then it was allowed to cool to rt and filtered through Celite, washing with $CH_2Cl_2$ (3×50 mL) and with 5% MeOH/$CH_2Cl_2$ (1×40 mL). The filtrate was concentrated to dryness and purified by flash column chromatography in silica gel (20% AcOEt/hexane), to yield 403 mg of the desired product (Rf=0.5 (20% AcOEt/hexane), pale yellow solid, 75% yield).

NMR-$^1$H (CDCl$_3$, 250 MHz, δ): 9.98 (s, 1H, CHO); 7.65 (d, J=2.5 Hz, 1H, ArH); 7.61 (d, J=8.5 Hz, 1H, ArH); 7.36 (dd, J=2.5 and 8.5 Hz, 1H, ArH); 6.73 (s, 1H, ArH); 2.39 (s, 3H, CH$_3$).

3.4 Synthesis of 4-(2-iodoethyl)morpholine

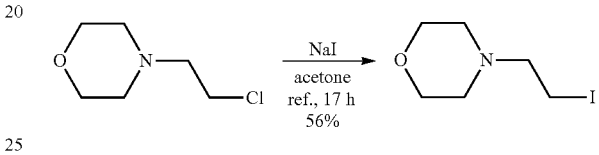

NaI (25.54 g, 170.40 mmol) was added over a suspension of the starting chloride (8.5 g, 56.80 mmol) in acetone (150 mL). The mixture was refluxed for 17 h, then it was allowed to cool to r.t. and filtered, washing with $CH_2Cl_2$ (3×100 mL). The filtrate was washed with $H_2O$ (3×250 mL), the organic phase was dried over $Na_2SO_4$ anh., filtered and concentrated to dryness to yield 7.71 g of the desired iodide (Rf=0.4 (40% AcOEt/hexane), oily yellow solid, 56% yield).

NMR-$^1$H (CDCl$_3$, 250 MHz, δ): 3.64 (t, J=4.7 Hz, 4H, CH$_2$); 3.14 (t, J=7.6 Hz, 2H, CH$_2$) 2.65 (t, J=7.6 Hz, 2H, CH$_2$) 2.42 (t, J=4.7 Hz, 4H, CH$_2$).

3.5 Synthesis of (4-ethylmorpholine)(triphenyl)phosphonium iodide

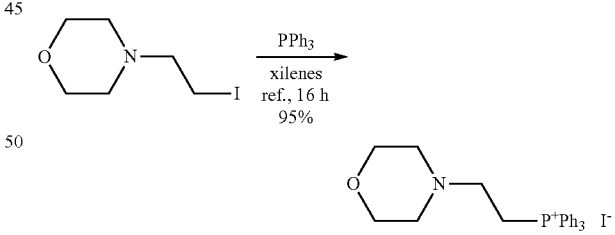

PPh$_3$ (3.26 g, 12.44 mmol) was added over a solution of the starting iodide (2.0 g, 8.29 mmol) in xylenes (15 mL). The mixture was refluxed for 16 h and then it was allowed to cool to rt. Toluene was added (8 mL) and it was stirred at rt for 2 h. The solid was filtered under vacuum, it was washed with Et$_2$O (3×10 mL) and dried, to yield 3.96 g of the desired product (Rf=0.1 (10% MeOH/CH$_2$Cl$_2$), white solid, 95% yield).

NMR-$^1$H (CDCl$_3$, 250 MHz, δ): 7.93-7.83 (m, 15H, ArH); 3.84 (m, 2H, CH$_2$); 3.29 (m, 4H, CH$_2$) 2.59 (m, 2H, CH$_2$) 2.30 (m, 4H, CH$_2$).

MS-EI+m/z: 376.0 (M−I).

3.6 Synthesis of 4-{3-[1-(3,4-dichlorophenyl)-5-methyl-1H-pyrazol-3-yl]prop-2-enyl}morpholine

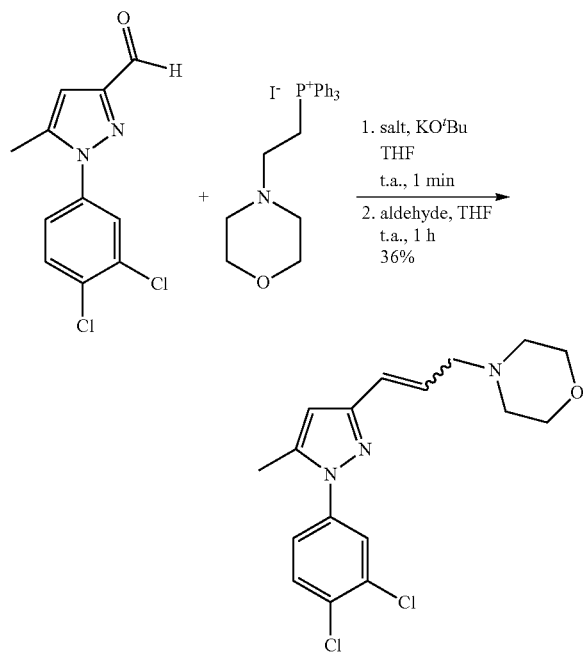

A portion of KOᵗBu (79 mg, 0.703 mmol) was added over a suspension of the phosphine salt (177 mg, 0.353 mmol) in THF (3 mL). It was stirred at r.t. for about 1 min (bright yellow suspension), and the starting aldehyde (108 mg, 0.423 mmol) in THF (3 mL) was added. The reaction mixture was stirred at r.t. for 1 h, and then diluted with CH$_2$Cl$_2$ (10 mL) and H$_2$O (10 mL) was added. The organic phase was separated and the aqueous phase was extracted with CH$_2$Cl$_2$ (1×10 mL). The combined organic phases were dried over Na$_2$SO$_4$ anh., filtered and concentrated to dryness. The residue was purified by three consecutive flash column chromatography in silica gel (4% MeOH/CH$_2$Cl$_2$, 50% acetone/Hexane and CH$_2$Cl$_2$/MeOH/NH$_4$OH 98:2:1) to yield 45 mg of the desired product (Rf=0.5 (50% acetone/Hexane), pale yellow oil, 36% yield).

NMR-$^1$H (CDCl$_3$, 250 MHz, δ) major isomer: 7.62 (d, J=2.5 Hz, 1H, ArH); 7.54 (d, J=8.5 Hz, 1H, ArH); 7.33 (dd, J=2.5 and 8.5 Hz, 1H, ArH); 6.45 (d, J=11.8 Hz, 1H, CH); 6.22 (s, 1H, ArH); 5.84 (m, 1H, CH); 3.74 (m, 4H, CH$_2$); 3.46 (dd, J=1.9 and 6.3 Hz, 2H, CH$_2$); 2.53 (m, 4H, CH$_2$); 2.37 (s, 3H, CH$_3$).

MS-EI+m/z: 352.0, 354.0 (M).

3.7 Synthesis of 4-{3-[1-(3,4-dichlorophenyl)-5-methyl-1H-pyrazol-3-yl]propyl}morpholine

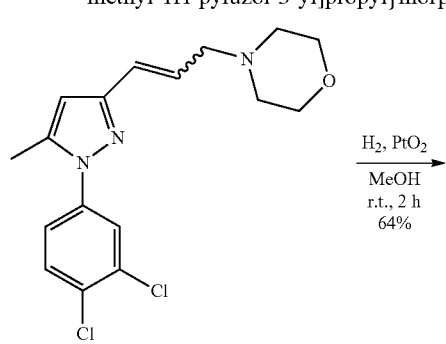

PtO$_2$ (4 mg, 0.017 mmol) was added over a solution of a solution of the starting material (123 mg, 0.349 mmol) in MeOH (4 mL). The suspension was stirred at r.t. under H$_2$ atmosphere (balloon) for 2 h, and then it was filtered through Celite, washing with MeOH (3×5 mL). The filtrate was concentrated to dryness and purified by flash column chromatography in silica gel (40% acetone/Hexane) to yield 79 mg of the desired product (Rf=0.4 (50% acetone/Hexane), pale yellow oil, 64% yield).

NMR-$^1$H (CDCl$_3$, 250 MHz, δ): 7.59 (d, J=2.5 Hz, 1H, ArH); 7.50 (d, J=8.8 Hz, 1H, ArH); 7.29 (dd, J=2.5 and 8.8 Hz, 1H, ArH); 6.02 (s, 1H, ArH); 3.72 (m, 4H, CH$_2$); 2.64 (t, J=7.7 Hz, 2H, CH$_2$); 2.44 (m, 6H, CH$_2$); 2.32 (s, 3H, CH$_3$); 1.87 (m, 2H, CH$_2$).

MS-EI+m/z: 351.8, 353.8 (M).

Example 4

Synthesis of 4-{3-[5-Methyl-1-(2-naphthyl)-1H-pyrazol-3-yl]propyl}morpholine

4.1 Synthesis of 2-naphthylhydrazine hydrochloride

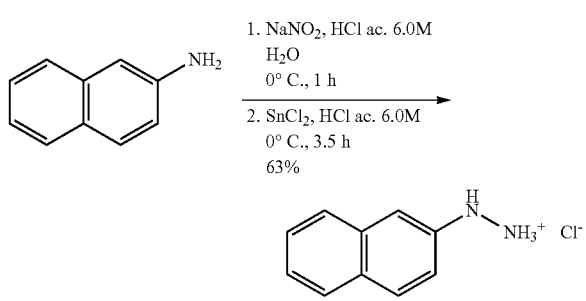

NaNO$_2$ (578 mg, 8.38 mmol) in H$_2$O (1.2 mL) was slowly added (2 min of addition) over a suspension of 2-naphthylamine (800 mg, 5.59 mmol) in HCl ac. 6.0 M (6 mL) cooled in a H$_2$O-ice bath. The resulting solution was stirred in H$_2$O-ice bath for 1 h, and SnCl$_2$ (3.71 g, 19.56 mol) was slowly added (5 min of addition). The resulting suspension was stirred in H$_2$O-ice bath for 3.5 h, and then it was filtered. The solid was washed with H$_2$O at 0° C. (4×8 mL), with H$_2$O at rt (1×8 mL), with Et$_2$O at 0° C. (2×4 mL), with Et$_2$O/hexane (1:1, 2×4 mL) and with hexane (2×5 mL). The solid was dried to yield 690 mg of the desired product (Rf=0.7 (40% AcOEt/hexane), cream solid, 63% yield).

NMR-$^1$H (DMSO-d$_6$, 250 MHz, δ): 7.81 (m, 2H, ArH); 7.71 (d, J=7.7 Hz, 1H, ArH); 7.49-7.19 (m, 4H, ArH).

MS-EI+m/z: 159.1 (M−HCl+1).

4.2 Synthesis of ethyl 5-methyl-1-(2-naphthyl)-1H-pyrazole-3-carboxylate

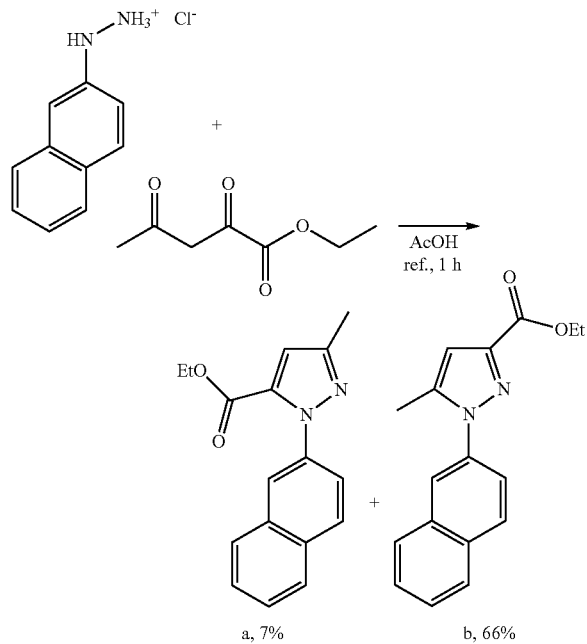

Ethyl acetopyruvate (544 mg, 3.44 mmol) was added over a suspension of the starting hydrazine (670 mg, 3.44 mmol) in AcOH (5 mL). The resulting suspension was refluxed for 1 h and then it was allowed to cool to rt and diluted with $CH_2Cl_2$ (15 mL). The organic phase was washed with $H_2O$ (2×20 mL), with NaOH ac. 10% (1×20 mL) and again with $H_2O$ (1×20 mL). The organic phase was dried over $Na_2SO_4$ anh., filtered and concentrated to dryness. The crude was purified by flash column chromatography in silica gel (15-41% AcOEt/hexane), to yield 68 mg of isomer a (Rf=0.8 (20% AcOEt/hexane), orange solid, 7% yield) and 640 mg of isomer b (Rf=0.6 (20% AcOEt/hexane), orange solid, 66% yield).

NMR-$^1$H isomer b ($CDCl_3$, 250 MHz, δ): 7.95-7.84 (m, 4H, ArH); 7.60-7.51 (m, 3H, ArH); 6.78 (s, 1H, ArH); 4.43 (c, J=7.1 Hz, 2H, $CH_2$); 2.38 (s, 3H, $CH_3$); 1.40 (t, J=7.1 Hz, 3H, $CH_3$).

NMR-$^1$H isomer a ($CDCl_3$, 250 MHz, δ): 7.91-7.85 (m, 4H, ArH); 7.53-7.48 (m, 3H, ArH); 6.86 (s, 1H, ArH); 4.22 (c, J=7.1 Hz, 2H, $CH_2$); 2.39 (s, 3H, $CH_3$); 1.20 (t, J=7.1 Hz, 3H, $CH_3$).

4.3 Synthesis of [5-methyl-1-(2-naphthyl)-1H-pyrazol-3-yl]methanol

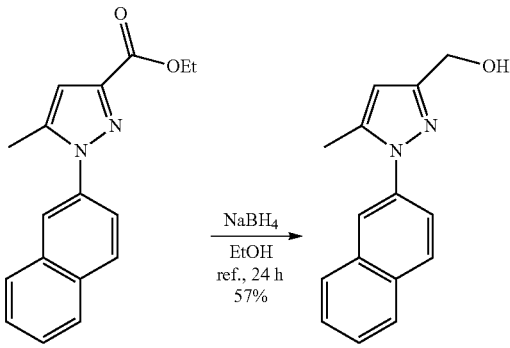 [SMILES: CCOC(=O)c1cc(C)n(-c2ccc3ccccc3c2)n1 ; "NaBH4" ; Cc1cc(CO)nn1-c1ccc2ccccc2c1]

$NaBH_4$ (129 mg, 3.42 mmol) was added over a suspension of the starting ester (640 mg, 2.28 mmol) in EtOH (15 mL). The mixture was refluxed (it dissolves when refluxing) for 1.5 h, and then more $NaBH_4$ (640 mg, 2.28 mmol) was added. It was refluxed for 4 h more, and more $NaBH_4$ (640 mg, 2.28 mmol) was added. After 2.5 h, more $NaBH_4$ (640 mg, 2.28 mmol) was added and it was refluxed for 16 h more. The reaction mixture was allowed to cool to r.t. and poured into $H_2O$ (10 mL). The aqueous phase was extracted with $CH_2Cl_2$ (2×15 mL) and the combined organic phases were washed with $NH_4Cl$ ac. sat. (2×30 mL), dried over $Na_2SO_4$ anh., filtered and concentrated to dryness. The crude was purified by flash column chromatography in silica gel (60-70% AcOEt/hexane), to yield 309 mg of the desired product (R/0.2 (40% AcOEt/hexane), yellow solid, 57% yield).

NMR-$^1$H ($CDCl_3$, 250 MHz, δ): 7.96-7.96 (m, 4H, ArH); 7.61 (d, J=1.9 Hz, 1H, ArH); 7.56 (m, 2H, ArH); 6.25 (s, 1H, ArH); 4.74 (sa, 2H, $CH_2$); 2.39 (s, 3H, $CH_3$).

4.4 Synthesis of 5-methyl-1-(2-naphthyl)-1H-pyrazole-3-carbaldehyde

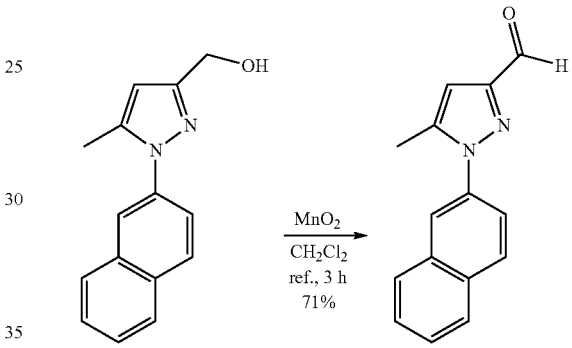

$MnO_2$ (85% assay, 1.33 g, 12.97 mmol) was added over a solution of the starting alcohol (309 mg, 1.29 mmol) in $CH_2Cl_2$ (10 mL). The mixture was refluxed for 3 h, and then it was allowed to cool to r.t. and filtered through Celite, washing with $CH_2Cl_2$ (2×15 mL) and with 10% MeOH/$CH_2Cl_2$ (3×15 mL). The filtrate was concentrated to dryness and purified by flash column chromatography in silica gel (20% AcOEt/hexane), to yield 218 mg of the desired product (Rf=0.8 (40% AcOEt/hexane), pale yellow solid, 71% yield).

NMR-$^1$H ($CDCl_3$, 250 MHz, δ): 10.04 (s, 1H, CHO); 7.94 (m, 4H, ArH); 7.60 (m, 3H, ArH); 6.77 (s, 1H, ArH); 2.43 (s, 3H, CH3).

4.5 Synthesis of 4-{3-[5-methyl-1-(2-naphthyl)-1H-pyrazol-3-yl]prop-2-enyl}morpholine

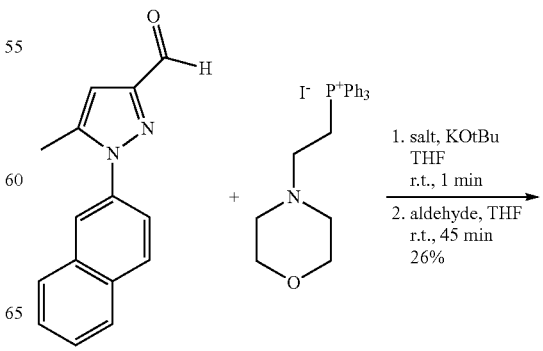

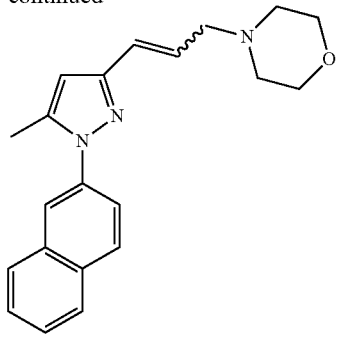

A portion of KOtBu (69 mg, 0.6214 mmol) was added over a suspension of the phosphine salt (154 mg, 0.307 mmol) in THF (3 mL). It was stirred for about 1 min (bright yellow suspension), and the starting aldehyde (87 mg, 0.368 mmol) was added in THF (2 mL). The reaction mixture was stirred at it for 45 min, and then NH$_4$Cl ac. sat. (10 mL) was added and extracted with AcOEt (1×10 mL). The organic phase was washed with NH$_4$Cl ac. sat. (2×10 mL) and with H$_2$O (1×10 mL), dried over Na$_2$SO$_4$ anh., filtered and concentrated to dryness. The crude was purified by flash column chromatography in silica gel (3% MeOH/CH$_2$Cl$_2$) to yield 27 mg of the desired product (Rf=0.2 (5% MeOH/CH$_2$Cl$_2$), yellow oil, 26% yield).

NMR-$^1$H (CDCl$_3$, 250 MHz, δ) major isomer: 7.88 (m, 4H, ArH); 7.62 (dd, J=2.0 and 8.6 Hz, 1H, ArH); 7.55 (m, 2H, ArH); 6.54 (d, J=11.8 Hz, 1H, CH); 6.27 (s, 1H, ArH); 5.84 (m, 1H, CH); 3.80 (m, 4H, CH$_2$); 3.51 (m, 2H, CH$_2$); 2.57 (m, 4H, CH$_2$); 2.42 (s, 3H, CH$_3$).

4.6 Synthesis of 4-{3-[5-Methyl-1-(2-naphthyl)-1H-pyrazol-3-yl]propyl}morpholine

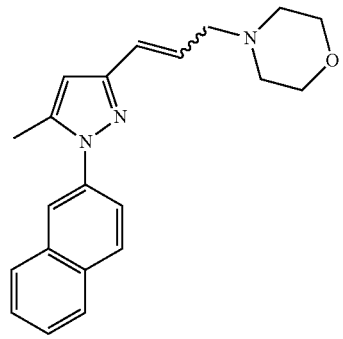

The starting material (57 mg, 0.171 mmol) in MeOH (4 mL) was added over a suspension of Pd/C (10% by weight, 18 mg, 0.017 mmol) in MeOH (4 mL). The resulting suspension was stirred at rt under H$_2$ atmosphere (balloon) for 2.5 h, and then it was filtered through Celite, washing with MeOH (3×5 mL). The filtrate was concentrated to dryness and purified by flash column chromatography in silica gel (3% MeOH/CH$_2$Cl$_2$) to yield 46 mg of the desired product (Rf=0.15 (5% MeOH/CH$_2$Cl$_2$), yellow oil, 81% yield).

NMR-$^1$H (CDCl$_3$, 250 MHz, δ): 7.84-7.94 (m, 4H, ArH); 7.59 (dd, J=2.2 and 8.8 Hz, 1H, ArH); 7.52 (m, 2H, ArH); 6.06 (s, 1H, ArH); 3.74 (m, 4H, CH$_2$); 2.71 (t, J=7.7 Hz, 2H, CH$_2$); 2.49 (m, 6H, CH$_2$); 2.38 (s, 3H, CH$_3$); 1.91 (m, 2H, CH$_2$).

MS-EI+m/z: 335.9 (M+1).

Example 5

Synthesis of 4-(2-{2-[1-(3,4-dichlorophenyl)-5-methyl-1H-pyrazol-3-yl]ethoxy)ethyl}morpholine

5.1. Synthesis of 1-(3,4-dichlorophenyl)-3-[2-methoxyvinyl]-5-methyl-1H-pyrazole

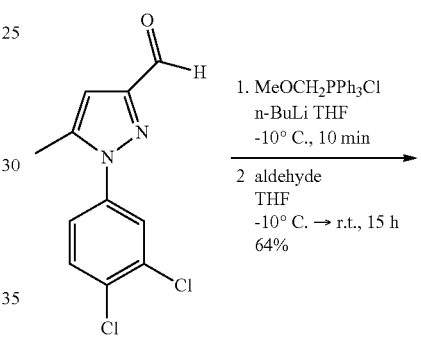

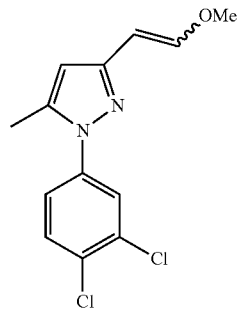

Over a suspension of (methoxymethyl)-triphenylphosphonium chloride (2.06 g, 6.0 mmol) in THF (10 mL) cooled at −35° C. in a CO$_2$-acetone bath, was slowly added n-BuLi (2.5 M in hexane, 2.4 mL, 6.0 mmol; 20 min of addition). The mixture was stirred, it was allowed to cool to −10° C. for 10 min, and the starting aldehyde (770 mg, 3.02 mmol) in THF (5.0 mL) was added slowly. The mixture was allowed to cool to r.t. and it was stirred for 15 h and poured into NH$_4$Cl ac. sat. (30 mL). The aqueous phase was extracted with AcOEt (1×30 mL). The organic phases were washed with NH$_4$Cl ac. sat. (1×30 mL) and with H$_2$O (1×20 mL), dried over Na$_2$SO$_4$ anti., filtered and concentrated to dryness. The crude was purified by flash column chromatography in Biotage SP1 (0-30% AcOEt/hexane), to yield 550 mg of the desired product (Rf=0.5 (20% AcOEt/hexane), yellow oil, 64% yield).

NMR-$^1$H (CDCl$_3$, 250 MHz, δ): 7.61 (d, J=2.5 Hz, 1H, ArH); 7.50 (d, J=8.5 Hz, 1H, ArH); 7.31 (dd, J=8.5 and 2.5 Hz, 1H, ArH); 7.17 (d, J=13.2 Hz, 0.5H, CH); 6.59 (s, 0.5H, ArH); 6.22 (d, J=6.9 Hz, 0.5H, CH); 6.13 (s, 0.5H, ArH); 5.78 (d, J=13.2 Hz, 0.5H, CH); 5.45 (d, J=6.9 Hz, 0.5H, CH); 3.80 (s, 1.5H, CH₃); 3.68 (s, 1.5H, CH₃); 2.35 (s, 1.5H, CH₃); 2.33 (s, 1.5H, CH₃).

MS-EI+m/z: 282.6, 285.3 (M+1).

5.2 Synthesis of [1-(3,4-dichlorophenyl)-5-methyl-1H-pyrazol-3-yl]acetaldehyde

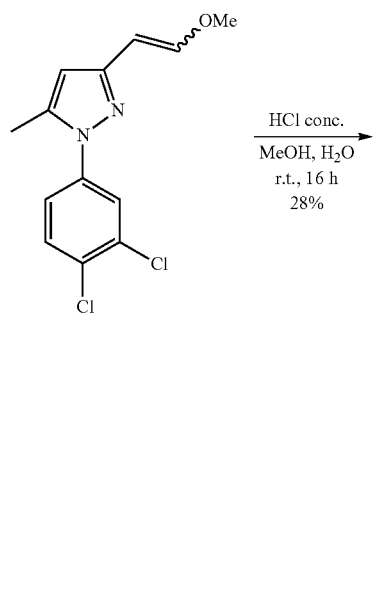

H₂O (1.0 mL) and HCl conc. (2.3 mL) was added over a solution of the starting ester (400 mg, 1.41 mmol) in MeOH (4.0 mL). The mixture was stirred at rt atmosphere for 16 h. NaOH ac. 50% was added to pH 7-8, and the aqueous phase was extracted with AcOEt (4×15 mL). The combined organic phases dried over Na₂SO₄ anh., filtered and concentrated to dryness. The crude was purified by Biotage SP1 (0-30% AcOEt/hexane) to yield 106 mg of the desired product (Rf=0.3 (20% AcOEt/hexane), yellow oil, 28% yield).

NMR-¹H (CDCl₃, 250 MHz, δ): 9.76 (t, J=1.9 Hz, 1H, CHO); 7.56 (d, J=2.5 Hz, 1H, ArH); 7.49 (d, J=8.5 Hz, 1H, ArH); 7.27 (dd, J=8.5 and 2.5 Hz, 1H, ArH); 6.11 (s, 1H, ArH); 3.68 (d, J=1.9 Hz, 2H, CH₂); 2.31 (s, 3H, CH₃).

5.3 Synthesis of 2-[1-(3,4-dichlorophenyl)-5-methyl-1H-pyrazol-3-yl]ethanol

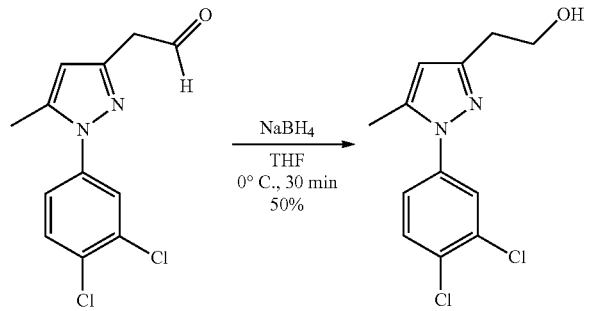 [SMILES: Cc1cc(CC=O)nn1-c1ccc(Cl)c(Cl)c1 ; "NaBH4" ; Cc1cc(CCO)nn1-c1ccc(Cl)c(Cl)c1]

NaBH₄ (92 mg, 2.43 mmol) was added over a solution of the starting aldehyde (219 mg, 0.814 mmol) in THF (5.0 mL) cooled in a H₂O-ice bath. The resulting solution was stirred in H₂O-ice bath for 30 min, and poured into NH₄Cl ac. sat. (15 mL). The aqueous phase was extracted with AcOEt (2×15 mL) and the combined organic phases were dried over Na₂SO₄ anh., filtered and concentrated to dryness. The crude was purified by Biotage SP1 (0-60% AcOEt/hexane), to yield 110 mg of the desired product (Rf=0.3 (40% AcOEt/hexane), solid white, 50% yield).

NMR-¹H (CDCl₃, 250 MHz, δ): 7.58 (d, J=2.5 Hz, 1H, ArH); 7.52 (d, J=8.5 Hz, 1H, ArH); 7.30 (dd, J=8.5 and 2.5 Hz, 1H, ArH); 6.07 (s, 1H, ArH); 3.91 (m, 2H, CH₂); 2.87 (t, J=5.9 Hz, 2H, CH₂); 2.34 (s, 3H, CH₃).

5.4 Synthesis of 4-(2-{2-[1-(3,4-dichlorophenyl)-5-methyl-1H-pyrazol-3-yl]ethoxy}ethyl)morpholine

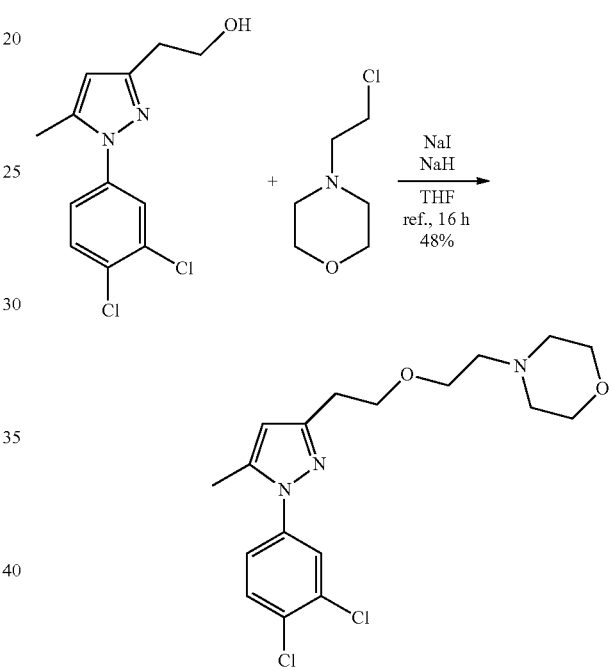

NaH (60% in mineral oil, 30 mg, 0.76 mmol) was added over a solution of the starting alcohol (104 mg, 0.383 mmol) in THF (5 mL). The mixture was stirred at rt for 10 min, and 4-(2-chloroethyl)morpholine (69 mg, 0.461 mmol) and NaI (74 mg, 0.493 mmol) were added. The reaction mixture was refluxed for 16 h, then it was allowed to cool to r.t. and poured into H₂O (10 mL). The aqueous phase was extracted with AcOEt (3×15 mL) and the combined organic phases were dried over Na₂SO₄ anh., filtered and concentrated to dryness. The residue was purified by Biotage SP1 (4-15% MeOH/CH₂Cl₂), to yield 70 mg of the desired product (Rf=0.2 (5% MeOH/CH₂Cl₂), orange oil, 48% yield).

NMR-¹H (CDCl₃, 250 MHz, δ): 7.59 (d, J=2.5 Hz, 1H, ArH); 7.51 (d, J=8.5 Hz, 1H, ArH); 7.29 (dd, J=8.5 and 2.5 Hz, 1H, ArH); 6.09 (s, 1H, ArH); 3.76-3.68 (m, 6H, CH₂); 3.62 (t, J=5.8 Hz, 2H, CH₂); 2.91 (t, J=7.0 Hz, 2H, CH₂); 2.59 (t, J=5.8 Hz, 2H, CH₂); 2.49 (m, 4H, CH₂); 2.33 (s, 3H, CH₃).

MS-EI+m/z: 384.2; 386.0 (M+1).

Further compounds of the invention are the examples shown in the following table:

| Example | Structure | Name | NMR |
|---|---|---|---|
| 6 | 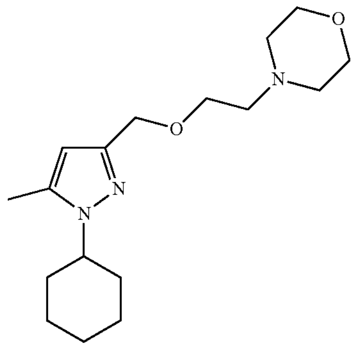 [SMILES: Cc1cc(COCCN2CCOCC2)nn1C1CCCCC1] | 4-(2-((1-cyclohexyl-5-methyl-1H-pyrazol-3-yl)methoxy)ethyl)-morpholine | $^1$H NMR (CDCl$_3$) δ ppm: 5.98 (s, 1H), 4.47 (s, 2H), 4.00-3.80 (m, 1H), 3.80-3.67 (m, 4H), 3.61 (t, J = 5.8 Hz, 2H), 2.60 (t, J = 5.8 Hz, 2H), 2.54-2.41 (m, 4H), 2.24 (s, 3H), 1.99-1.80 (m, 6H), 1.52-1.15 (m, 4H). |
| 7 | 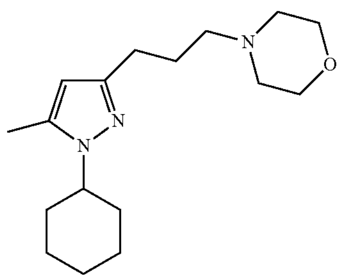 [SMILES: Cc1cc(CCCN2CCOCC2)nn1C1CCCCC1] | 4-(3-(1-cyclohexyl-5-methyl-1H-pyrazol-3-yl)propyl)morpholine | $^1$H NMR (CDCl$_3$) δ ppm: 5.76 (s, 1H), 3.95-3.76 (m, 1H), 3.76-3.64 (m, 4H), 2.58 (t, J = 7.7 Hz, 2H), 2.49-2.32 (m, 6H), 2.22 (s, 3H), 1.99-1.64 (m, 9H), 1.49-1.17 (m, 3H). |
| 8 | 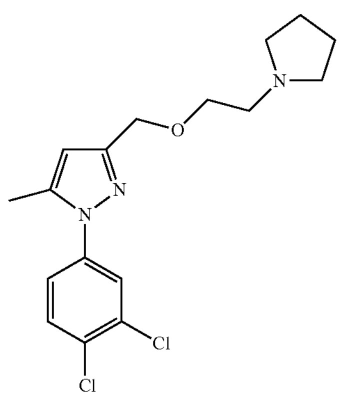 [SMILES: Cc1cc(COCCN2CCCC2)nn1-c1ccc(Cl)c(Cl)c1] | 1-(3,4-dichlorophenyl)-5-methyl-3-((2-(pyrrolidin-1-yl)ethoxy)methyl)-1H-pyrazole | $^1$H NMR (CDCl$_3$) δ ppm: 7.60 (d, J = 1.8 Hz, 1H), 7.53 (d, J = 8.6 Hz, 1H), 7.31 (dd, J = 8.6, 2.4 Hz, 1H), 6.25 (s, 1H), 4.55 (s, 2H), 3.64 (t, J = 6.0 Hz, 2H), 2.72 (t, J = 6.0 Hz, 2H), 2.56 (s, 4H), 2.35 (s, 3H), 1.90-1.57 (m, 4H). |
| 9 | 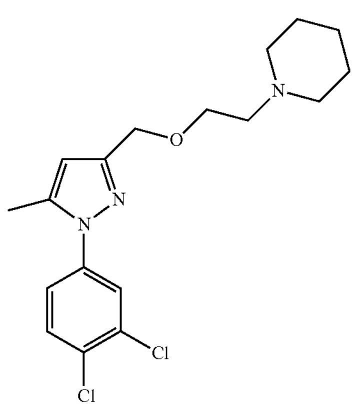 [SMILES: Cc1cc(COCCN2CCCCC2)nn1-c1ccc(Cl)c(Cl)c1] | 1-(2-((1-(3,4-dichlorophenyl)-5-methyl-1H-pyrazol-3-yl)methoxy)ethyl)-piperidine | $^1$H NMR (CDCl$_3$) δ ppm: 7.60 (d, J = 2.4 Hz, 1H), 7.52 (d, J = 8.6 Hz, 1H), 7.31 (dd, J = 8.6, 2.4 Hz, 1H), 6.25 (s, 1H), 4.53 (s, 2H), 3.64 (t, J = 6.1 Hz, 2H), 2.58 (t, J = 6.1 Hz, 2H), 2.48-2.38 (m, 4H), 2.34 (s, 3H), 1.65-1.50 (m, 4H), 1.50-1.37 (m, 2H). |

| Example | Structure | Name | NMR |
|---|---|---|---|
| 10 | 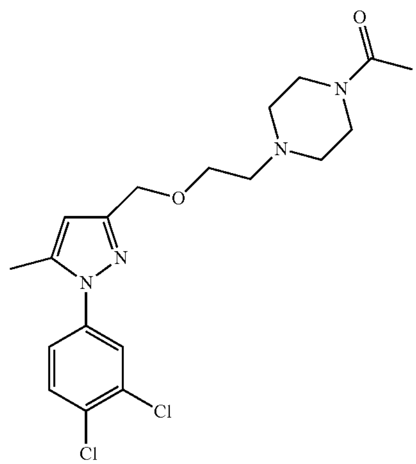 [SMILES: CC(=O)N1CCN(CCOCc2cc(C)n(-c3ccc(Cl)c(Cl)c3)n2)CC1] | 1-(4-(2-((1-(3,4-dichlorophenyl)-5-methyl-1H-pyrazol-3-yl)methoxy)ethyl)-piperazin-1-yl)-ethanone | $^1$H NMR (CDCl$_3$) δ ppm: 7.60 (d, J = 2.4 Hz, 1H), 7.52 (d, J = 8.6 Hz, 1H), 7.30 (dd, J = 8.6, 2.4 Hz, 1H), 6.25 (s, 1H), 4.55 (s, 2H), 3.64 (t, J = 6.1 Hz, 2H), 2.71 (t, J = 6.1 Hz, 2H), 2.61-2.49 (m, 4H), 2.34 (s, 3H), 1.84-1.72 (m, 4H), 1.78 (s, 3H). |
| 11 | 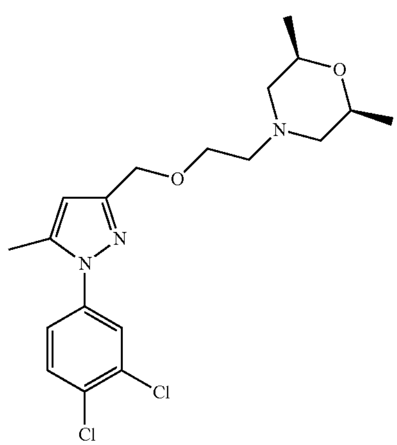 | (2S,6R)-4-(2-((1-(3,4-dichlorophenyl)-5-methyl-1H-pyrazol-3-yl)methoxy)ethyl)-2,6-dimethylmorpholine | $^1$H NMR (CDCl$_3$) δ ppm: 7.61 (d, J = 2.3 Hz, 1H), 7.55 (d, J = 8.6 Hz, 1H), 7.33 (d, J = 8.7 Hz, 1H), 6.20 (s, 1H), 4.56 (s, 2H), 4.40-4.23 (m, 2H), 4.14-4.00 (m, 2H), 3.56-3.39 (m, 2H), 3.29-3.09 (m, 2H), 2.61-2.41 (m, 2H), 2.35 (s, 3H), 1.18 (d, J = 5.8 Hz, 6H). |
| 12 | 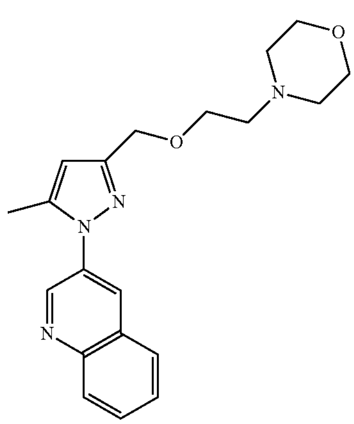 | 4-(2-((5-methyl-1-(quinolin-3-yl)-1H-pyrazol-3-yl)methoxy)ethyl)-morpholine | $^1$H NMR (CDCl$_3$) δ ppm: 9.07 (d, J = 2.5 Hz, 1H), 8.21 (d, J = 2.4 Hz, 1H), 8.17 (d, J = 8.6 Hz, 1H), 7.88 (d, J = 8.1 Hz, 1H), 7.85-7.70 (m, 1H), 7.68-7.52 (m, 1H), 6.32 (s, 1H), 4.60 (s, 2H), 3.78-3.65 (m, 6H), 2.64 (t, J = 5.8 Hz, 2H), 2.59-2.46 (m, 4H), 2.42 (s, 3H). |

-continued

| Example | Structure | Name | NMR |
|---|---|---|---|
| 13 | 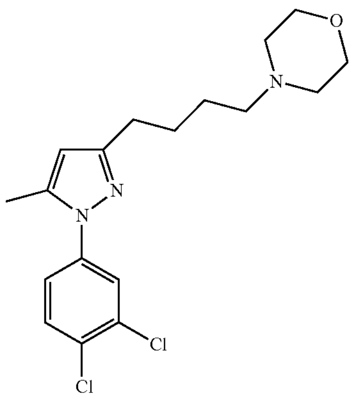 [SMILES: Cc1cc(CCCCN2CCOCC2)nn1-c1ccc(Cl)c(Cl)c1] | 4-(4-(1-(3,4-dichlorophenyl)-5-methyl-1H-pyrazol-3-yl)butyl)morpholine | $^1$H NMR (CDCl$_3$) δ ppm: 7.59 (d, J = 2.4 Hz, 1H), 7.51 (d, J = 8.6 Hz, 1H), 7.29 (dd, J = 8.7, 2.5 Hz, 1H), 6.02 (s, 1H), 3.89-3.60 (m, 4H), 2.82-2.37 (m, 8H), 2.33 (s, 3H), 1.90-1.39 (m, 4H). |
| 14 | 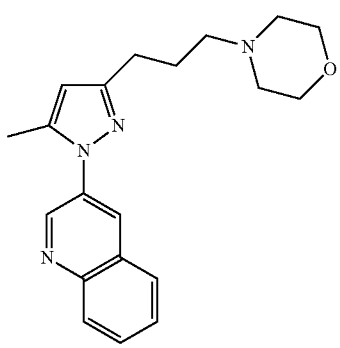 [SMILES: Cc1cc(CCCN2CCOCC2)nn1-c1cnc2ccccc2c1] | 4-(3-(5-methyl-1-(quinolin-3-yl)-1H-pyrazol-3-yl)propyl)morpholine | $^1$H NMR (CDCl$_3$) δ ppm: 9.07 (d, J = 2.4 Hz, 1H), 8.20 (d, J = 2.3 Hz, 1H), 8.16 (d, J = 8.6 Hz, 1H), 7.87 (dd, J = 8.2, 0.9 Hz, 1H), 7.80-7.71 (m, 1H), 7.65-7.56 (m, 1H), 6.11 (s, 1H), 4.00-3.65 (m, 4H), 2.89-2.62 (m, 2H), 2.59-2.46 (m, 6H), 2.41 (s, 3H), 2.03-1.87 (m, 2H). |
| 15 | 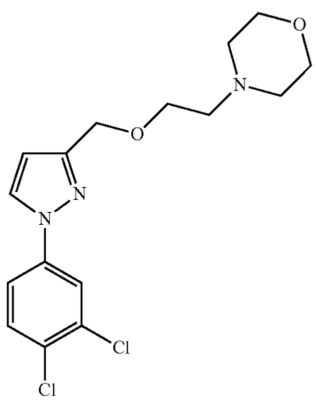 | 4-(2-((1-(3,4-dichlorophenyl)-1H-pyrazol-3-yl)methoxy)ethyl)-morpholine | $^1$H NMR (CDCl$_3$) δ ppm: 7.85-7.82 (m, 2H), 7.62-7.40 (m, 2H), 6.51 (d, J = 2.5 Hz, 1H), 4.62 (s, 2H), 3.77-3.69 (m, 4H), 3.66 (t, J = 5.7 Hz, 2H), 2.62 (t, J = 5.7 Hz, 2H), 2.55-2.46 (m, 4H). |
| 16 | 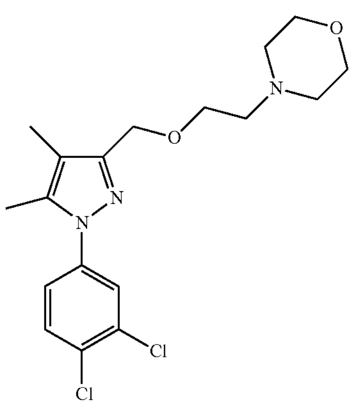 [SMILES: Cc1c(COCCN2CCOCC2)nn(-c2ccc(Cl)c(Cl)c2)c1C] | 4-(2-((1-(3,4-dichlorophenyl)-4,5-dimethyl-1H-pyrazol-3-yl)methoxy)ethyl)-morpholine | $^1$H NMR (CDCl$_3$) δ ppm: 7.56 (d, J = 2.3 Hz, 1H), 7.51 (d, J = 8.7 Hz, 1H), 7.28 (dd, J = 6.2, 2.0 Hz, 1H), 4.54 (s, 2H), 3.82-3.67 (m, 4H), 3.62 (t, J = 5.2 Hz, 2H), 2.60 (t, J = 5.5 Hz, 2H), 2.55-2.43 (m, 4H), 2.24 (s, 3H), 2.05 (s, 3H). |

| Example | Structure | Name | NMR |
|---|---|---|---|
| 17 | 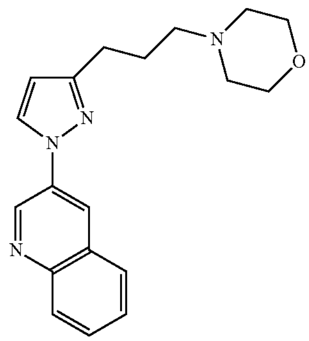 [SMILES: c1ccc2ncc(-n3ccc(CCCN4CCOCC4)n3)cc2c1] | 4-(3-(1-(quinolin-3-yl)-1H-pyrazol-3-yl)propyl)morpholine | $^1$H NMR (CDCl$_3$) δ ppm: 9.31 (d, J = 2.6 Hz, 1H), 8.37 (d, J = 2.3 Hz, 1H), 8.13 (d, J = 8.3 Hz, 1H), 8.00 (d, J = 2.5 Hz, 1H), 7.87 (d, J = 7.1 Hz, 1H), 7.77-7.65 (m, 1H), 7.65-7.51 (m, 1H), 6.37 (d, J = 2.4 Hz, 1H), 3.85-3.64 (m, 4H), 2.80 (t, J = 7.6 Hz, 2H), 2.56-2.40 (m, 6H), 2.06-1.86 (m, 2H). |
| 18 | 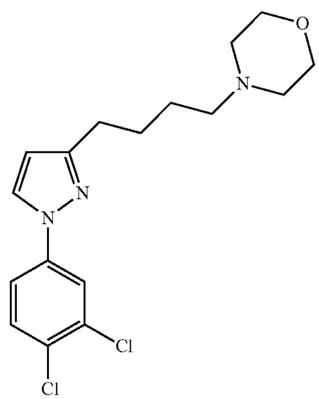 [SMILES: Clc1ccc(-n2ccc(CCCCN3CCOCC3)n2)cc1Cl] | 4-(4-(1-(3,4-dichlorophenyl)-1H-pyrazol-3-yl)butyl)morpholine | $^1$H NMR (CDCl$_3$) δ ppm: 7.81 (s, 1H), 7.77 (d, J = 2.4 Hz, 1H), 7.54-7.43 (m, 2H), 6.28 (d, J = 2.4 Hz, 1H), 3.87-3.60 (m, 4H), 2.72 (t, J = 7.4 Hz, 2H), 2.48-2.41 (m, 4H), 2.41-2.34 (m, 2H), 1.76-1.50 (m, 4H). |
| 19 | 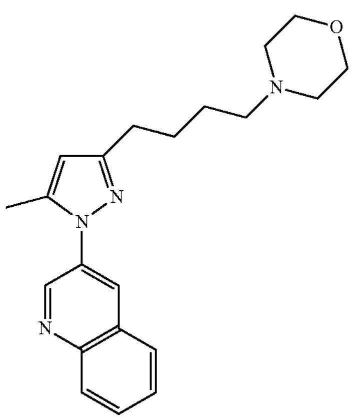 [SMILES: Cc1cc(CCCCN2CCOCC2)nn1-c1cnc2ccccc2c1] | 4-(4-(5-methyl-1-(quinolin-3-yl)-1H-pyrazol-3-yl)butyl)morpholine | $^1$H NMR (CDCl$_3$) δ ppm: 8.90 (d, J = 2.5 Hz, 1H), 8.03 (d, J = 2.5 Hz, 1H), 7.99 (d, J = 8.4 Hz, 1H), 7.70 (d, J = 8.1 Hz, 1H), 7.66-7.53 (m, 1H), 7.51-7.38 (m, 1H), 5.93 (s, 1H), 3.63-3.51 (m, 4H), 2.53 (t, J = 7.4 Hz, 2H), 2.36-2.26 (m, 4H), 2.23 (s, 3H), 1.64-1.39 (m, 4H). |
| 20 | 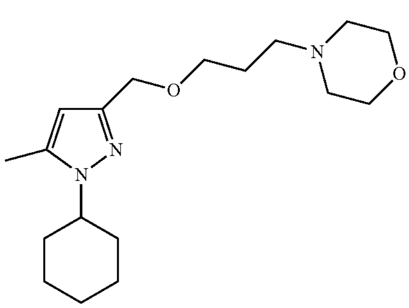 [SMILES: Cc1cc(COCCCN2CCOCC2)nn1C1CCCCC1] | 4-(3-((1-cyclohexyl-5-methyl-1H-pyrazol-3-yl)methoxy)propyl)-morpholine | $^1$H NMR (CDCl$_3$) δ ppm: 5.99 (s, 1H), 4.44 (s, 2H), 3.99-3.61 (m, 1H), 3.76-3.65 (m, 4H), 3.53 (t, J = 6.5 Hz, 2H), 2.51-2.36 (m, 6H), 2.25 (s, 3H), 1.98-1.63 (m, 8H), 1.47-1.18 (m, 2H). |

-continued

| Example | Structure | Name | NMR |
|---|---|---|---|
| 21 | 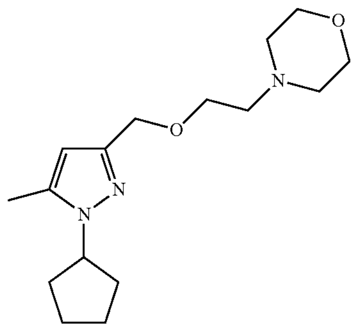 [SMILES: Cc1cc(COCCN2CCOCC2)nn1C1CCCC1] | 4-(2-((1-cyclopentyl-5-methyl-1H-pyrazol-3-yl)methoxy)ethyl)-morpholine | $^1$H NMR (CDCl$_3$) δ ppm: 5.99 (s, 1H), 4.47 (s, 2H), 3.77-3.67 (m, 4H), 3.60 (t, J = 5.8 Hz, 2H), 2.59 (t, J = 5.8 Hz, 2H), 2.54-2.40 (m, 4H), 2.25 (s, 3H), 2.10-1.96 (m, 4H), 1.96-1.83 (m, 2H), 1.76-1.55 (m, 2H). |
| 22 | 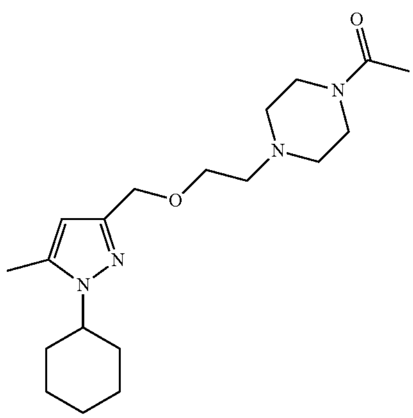 [SMILES: CC(=O)N1CCN(CCOCc2cc(C)n(C3CCCCC3)n2)CC1] | 1-(4-(2-((1-cyclohexyl-5-methyl-1H-pyrazol-3-yl)methoxy)ethyl)-piperazin-1-yl)ethanone hydrochloride | $^1$H NMR (DMSO-d$_6$) δ ppm: 6.00 (s, 1H), 4.42 (s, 2H), 4.08-3.96 (m, 1H), 3.87-3.79 (m, 2H), 3.52-3.35 (m, 4H), 3.34-3.25 (m, 2H), 3.32-2.95 (m, 4H), 2.25 (s, 3H), 2.04 (s, 3H), 1.88-1.64 (m, 7H), 1.48-1.34 (m, 2H), 1.30-1.14 (m, 1H). |
| 23 | 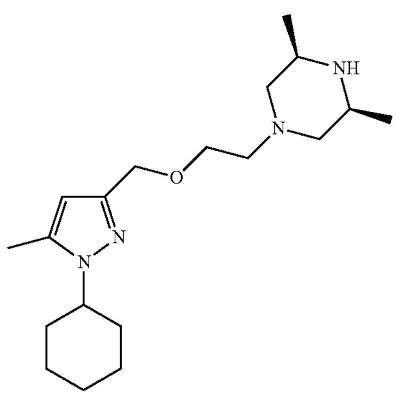 | (3S,5R)-1-(2-((1-cyclohexyl-5-methyl-1H-pyrazol-3-yl)methoxy)ethyl)-3,5-dimethylpiperazine hydrochloride | $^1$H NMR (DMSO-d$_6$) δ ppm: 5.93 (s, 1H), 4.30 (s, 2H), 4.09-3.91 (m, 1H), 3.58-3.43 (m, 2H), 3.23-3.08 (m, 2H), 3.03-2.87 (m, 2H), 2.23 (s, 3H), 2.14-1.94 (m, 2H), 1.88-1.71 (m, 4H), 1.73-1.57 (m, 2H), 1.50-1.03 (m, 6H), 1.19 (d, J = 5.7 Hz, 6H). |
| 24 | 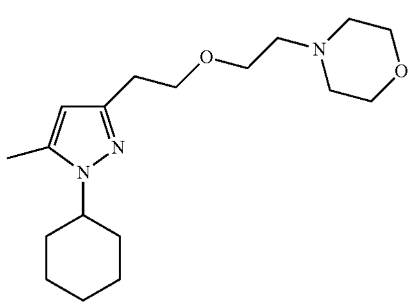 [SMILES: Cc1cc(CCOCCN2CCOCC2)nn1C1CCCCC1] | 4-(2-(2-(1-cyclohexyl-5-methyl-1H-pyrazol-3-yl)ethoxy)ethyl)-morpholine hydrochloride | $^1$H NMR (CDCl$_3$) δ ppm: 6.27 (s, 1H), 4.46-3.68 (m, 9H), 3.55-2.84 (m, 8H), 2.40 (s, 3H), 2.51-2.31 (m, 2H), 2.10-1.79 (m, 3H), 1.60-1.13 (m, 3H). |

-continued

| Example | Structure | Name | NMR |
|---|---|---|---|
| 25 | 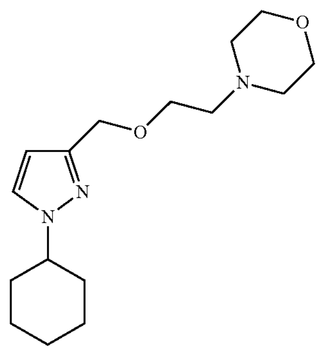 [SMILES: c1cn(C2CCCCC2)nc1COCCN1CCOCC1] | 4-(2-((1-cyclohexyl-1H-pyrazol-3-yl)methoxy)ethyl)-morpholine-hydrochloride | $^1$H NMR (CDCl$_3$) δ ppm: 7.64 (s, 1H), 6.52 (s, 1H), 4.84 (s, 2H), 4.79-4.61 (m, 2H), 4.37-4.12 (m, 4H), 4.09-3.87 (m, 2H), 3.69-3.36 (m, 4H), 3.32-3.00 (m, 1H), 2.45-2.22 (m, 2H), 2.05-1.86 (m, 2H), 1.85-1.63 (m, 3H), 1.63-1.39 (m, 2H), 1.39-1.13 (m, 1H). |
| 26 | 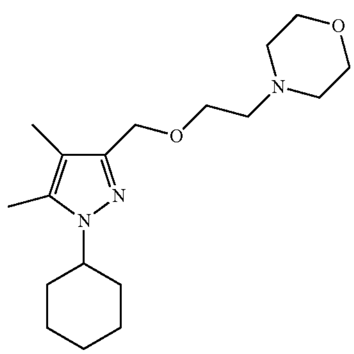 [SMILES: Cc1c(COCCN2CCOCC2)nn(C2CCCCC2)c1C] | 4-(2-((1-cyclohexyl-4,5-dimethyl-1H-pyrazol-3-yl)methoxy)ethyl)-morpholine hydrochloride | $^1$H NMR (CDCl$_3$) δ ppm: 4.62 (s, 2H), 4.24 (t, J = 12.0 Hz, 2H), 4.15-4.00 (m, 3H), 4.01-3.83 (m, 2H), 3.58-3.39 (m, 2H), 3.37-3.23 (m, 2H), 3.08 (t, J = 10.1 Hz, 2H), 2.23 (s, 3H), 2.15-2.03 (m, 2H), 1.99 (s, 3H), 2.04-1.79 (m, 4H), 1.77-1.57 (m, 1H), 1.52-1.28 (m, 3H). |
| 27 | 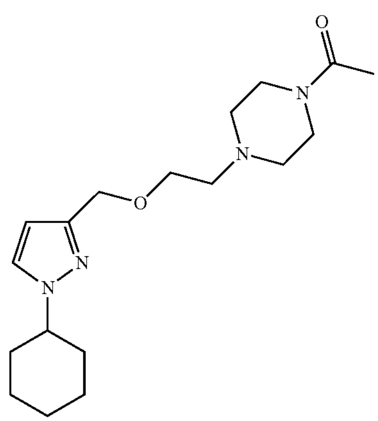 [SMILES: CC(=O)N1CCN(CCOCc2ccn(C3CCCCC3)n2)CC1] | 1-(4-(2-((1-cyclohexyl-1H-pyrazol-3-yl)methoxy)ethyl)-piperazin-1-yl)ethanone | |
| 28 | 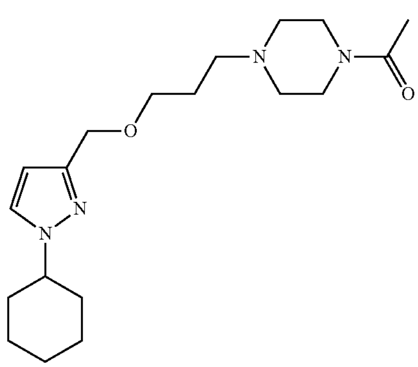 [SMILES: CC(=O)N1CCN(CCCOCc2ccn(C3CCCCC3)n2)CC1] | 1-(4-(3-((1-cyclohexyl-1H-pyrazol-3-yl)methoxy)propyl)-piperazin-1-yl)ethanone | |

| Example | Structure | Name | NMR |
|---------|-----------|------|-----|
| 29 | 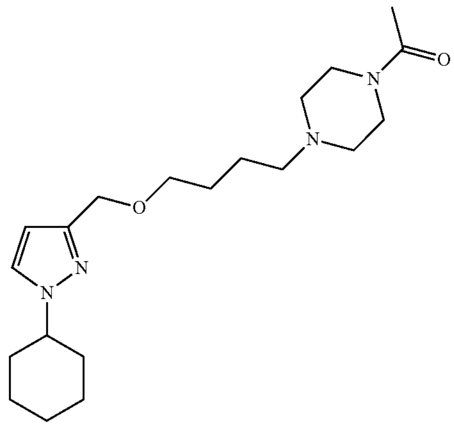 [SMILES: CC(=O)N1CCN(CCCCOCc2ccn(C3CCCCC3)n2)CC1] | 1-(4-(4-((1-cyclohexyl-1H-pyrazol-3-yl)methoxy)butyl)-piperazin-1-yl)ethanone | |
| 30 | 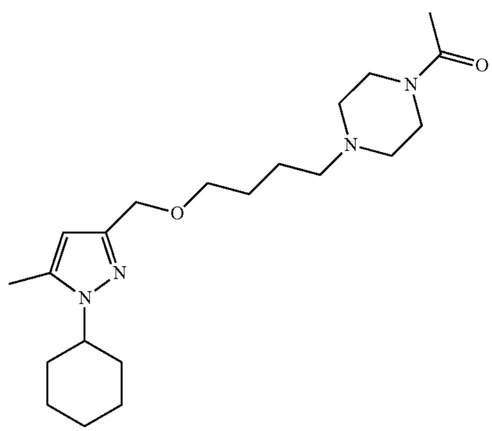 [SMILES: CC(=O)N1CCN(CCCCOCc2cc(C)n(C3CCCCC3)n2)CC1] | 1-(4-(4-((1-cyclohexyl-5-methyl-1H-pyrazol-3-yl)methoxy)butyl)-piperazin-1-yl)ethanone | |
| 31 | 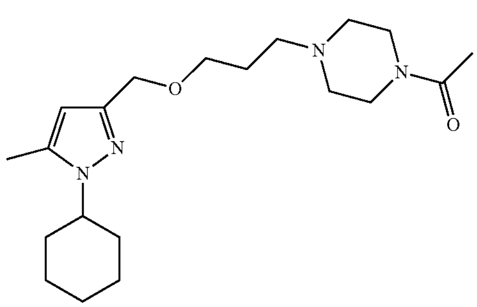 [SMILES: CC(=O)N1CCN(CCCOCc2cc(C)n(C3CCCCC3)n2)CC1] | 1-(4-(3-((1-cyclohexyl-5-methyl-1H-pyrazol-3-yl)methoxy)propyl)-piperazin-1-yl)ethanone | |

| Example | Structure | Name | NMR |
|---|---|---|---|
| 32 | 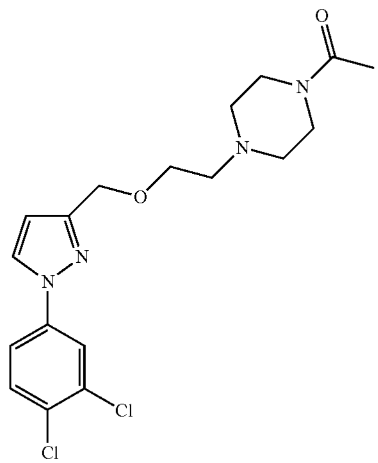 [SMILES: CC(=O)N1CCN(CCOCc2ccn(-c3ccc(Cl)c(Cl)c3)n2)CC1] | 1-(4-(2-((1-(3,4-dichlorophenyl)-1H-pyrazol-3-yl)methoxy)ethyl)-piperazin-1-yl)ethanone | |
| 33 | 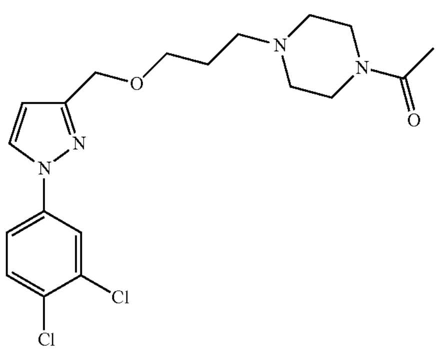 [SMILES: CC(=O)N1CCN(CCCOCc2ccn(-c3ccc(Cl)c(Cl)c3)n2)CC1] | 1-(4-(3-((1-(3,4-dichlorophenyl)-1H-pyrazol-3-yl)methoxy)propyl)-piperazin-1-yl)ethanone | |
| 34 | 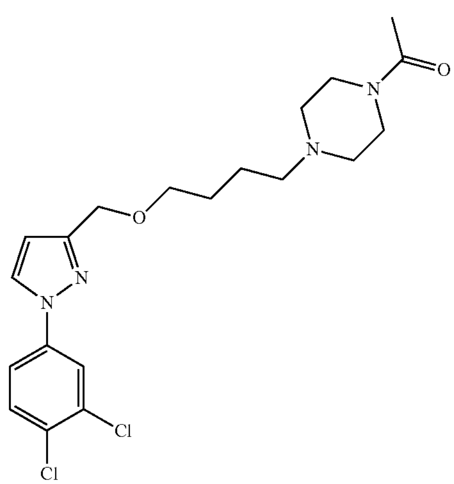 [SMILES: CC(=O)N1CCN(CCCCOCc2ccn(-c3ccc(Cl)c(Cl)c3)n2)CC1] | 1-(4-(4-((1-(3,4-dichlorophenyl)-1H-pyrazol-3-yl)methoxy)butyl)-piperazin-1-yl)ethanone | |

| Example | Structure | Name | NMR |
|---|---|---|---|
| 35 | 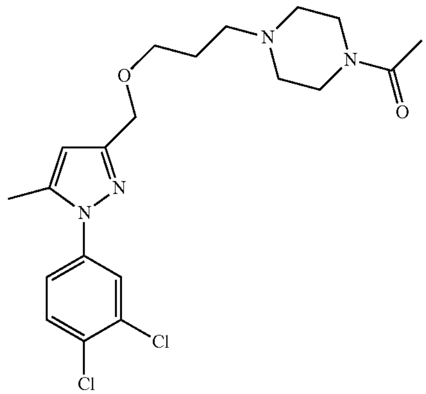 [SMILES: CC(=O)N1CCN(CCCOCc2cc(C)n(-c3ccc(Cl)c(Cl)c3)n2)CC1] | 1-(4-(3-((1-(3,4-dichlorophenyl)-5-methyl-1H-pyrazol-3-yl)methoxy)propyl)-piperazin-1-yl)ethanone | |
| 36 | 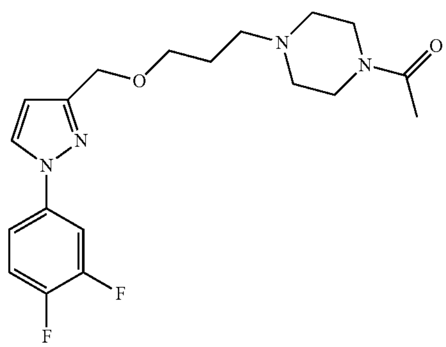 [SMILES: CC(=O)N1CCN(CCCOCc2ccn(-c3ccc(F)c(F)c3)n2)CC1] | 1-(4-(3-((1-(3,4-difluorophenyl)-1H-pyrazol-3-yl)methoxy)propyl)-piperazin-1-yl)ethanone | |
| 37 | 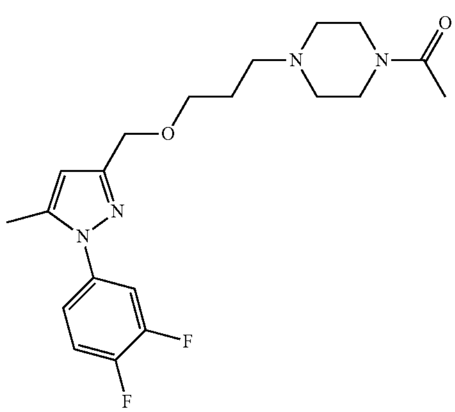 [SMILES: CC(=O)N1CCN(CCCOCc2cc(C)n(-c3ccc(F)c(F)c3)n2)CC1] | 1-(4-(3-((1-(3,4-difluorophenyl)-5-methyl-1H-pyrazol-3-yl)methoxy)propyl)-piperazin-1-yl)ethanone | |

-continued

| Example | Structure | Name | NMR |
|---|---|---|---|
| 38 | 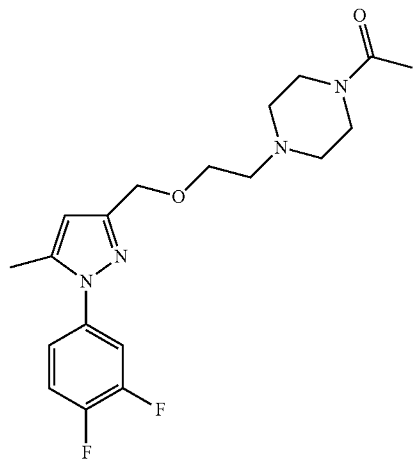 [SMILES: CC(=O)N1CCN(CCOCc2cc(C)n(-c3ccc(F)c(F)c3)n2)CC1] | 1-(4-(2-((1-(3,4-difluorophenyl)-5-methyl-1H-pyrazol-3-yl)methoxy)ethyl)-piperazin-1-yl)ethanone | |
| 39 | 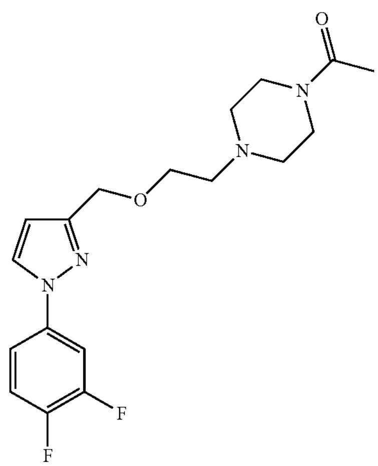 [SMILES: CC(=O)N1CCN(CCOCc2ccn(-c3ccc(F)c(F)c3)n2)CC1] | 1-(4-(2-((1-(3,4-difluorophenyl)-1H-pyrazol-3-yl)methoxy)ethyl)-piperazin-1-yl)ethanone | |
| 40 | 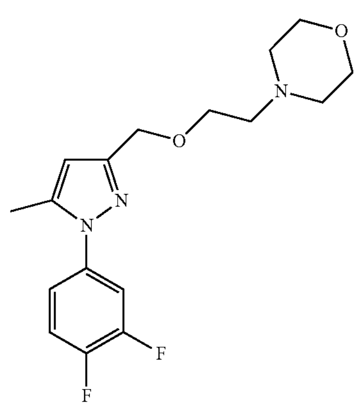 [SMILES: Cc1cc(COCCN2CCOCC2)nn1-c1ccc(F)c(F)c1] | 4-(2-((1-(3,4-difluorophenyl)-5-methyl-1H-pyrazol-3-yl)methoxy)ethyl)-morpholine | |

| Example | Structure | Name | NMR |
|---|---|---|---|
| 41 | 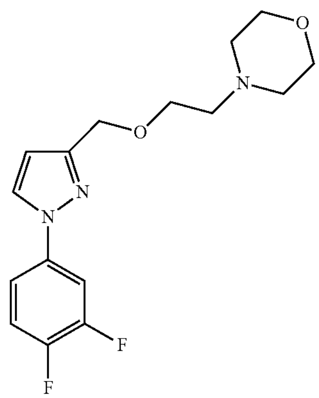 [SMILES: Fc1ccc(-n2ccc(COCCN3CCOCC3)n2)cc1F] | 4-(2-((1-(3,4-difluorophenyl)-1H-pyrazol-3-yl)methoxy)ethyl)morpholine | |
| 42 | 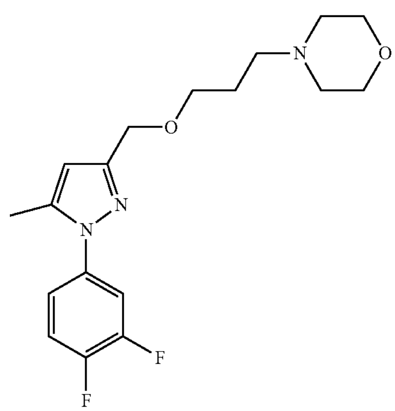 [SMILES: Cc1cc(COCCCN2CCOCC2)nn1-c1ccc(F)c(F)c1] | 4-(3-((1-(3,4-difluorophenyl)-5-methyl-1H-pyrazol-3-yl)methoxy)propyl)-morpholine | |
| 43 | 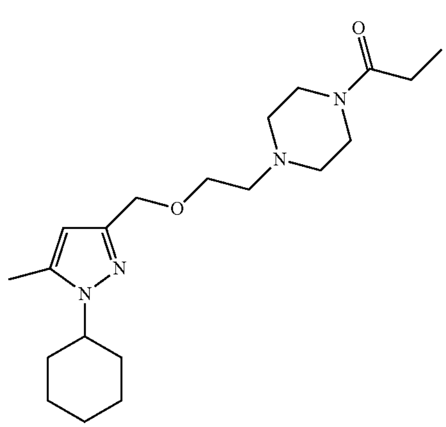 [SMILES: CCC(=O)N1CCN(CCOCc2cc(C)n(C3CCCCC3)n2)CC1] | 1-(4-(2-((1-cyclohexyl-5-methyl-1H-pyrazol-3-yl)methoxy)ethyl)-piperazin-1-yl)propan-1-one | |

-continued

| Example | Structure | Name | NMR |
|---|---|---|---|
| 44 | 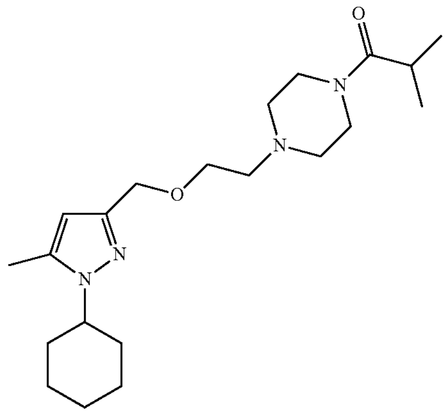 [SMILES: Cc1cc(COCCN2CCN(C(=O)C(C)C)CC2)nn1C1CCCCC1] | 1-(4-(2-((1-cyclohexyl-5-methyl-1H-pyrazol-3-yl)methoxy)ethyl)-piperazin-1-yl)-2-methylpropan-1-one | |
| 45 | 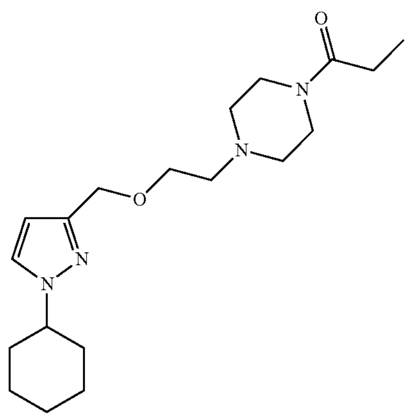 [SMILES: CCC(=O)N1CCN(CCOCc2ccn(C3CCCCC3)n2)CC1] | 1-(4-(2-((1-cyclohexyl-1H-pyrazol-3-yl)methoxy)ethyl)-piperazin-1-yl)propan-1-one | |
| 46 | 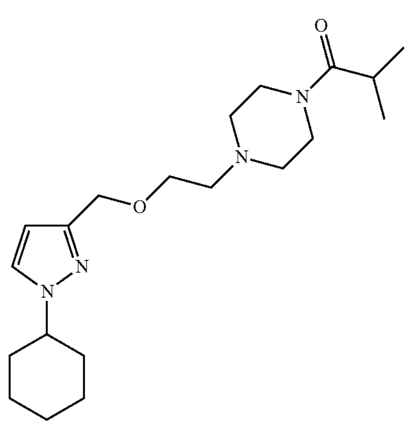 [SMILES: CC(C)C(=O)N1CCN(CCOCc2ccn(C3CCCCC3)n2)CC1] | 1-(4-(2-((1-cyclohexyl-1H-pyrazol-3-yl)methoxy)ethyl)-piperazin-1-yl)-2-methylpropan-1-one | |

| Example | Structure | Name | NMR |
|---|---|---|---|
| 47 | 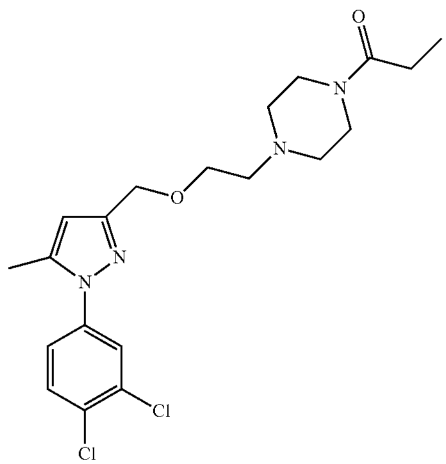 [SMILES: CCC(=O)N1CCN(CCOCc2cc(C)n(-c3ccc(Cl)c(Cl)c3)n2)CC1] | 1-(4-(2-((1-(3,4-dichlorophenyl)-5-methyl-1H-pyrazol-3-yl)methoxy)ethyl)-piperazin-1-yl)-propan-1-one | |
| 48 | 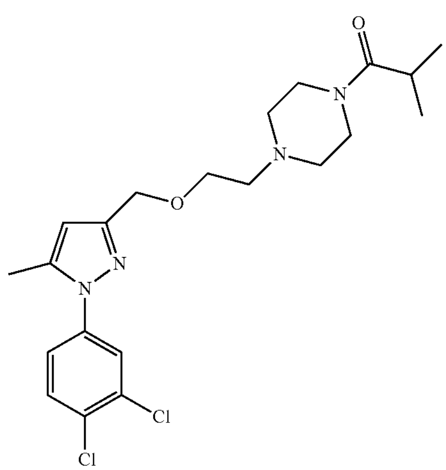 [SMILES: Cc1cc(COCCN2CCN(C(=O)C(C)C)CC2)nn1-c1ccc(Cl)c(Cl)c1] | 1-(4-(2-((1-(3,4-difluorophenyl)-5-methyl-1H-pyrazol-3-yl)methoxy)ethyl)-piperazin-1-yl)-2-methylpropan-1-one | |
| 49 | 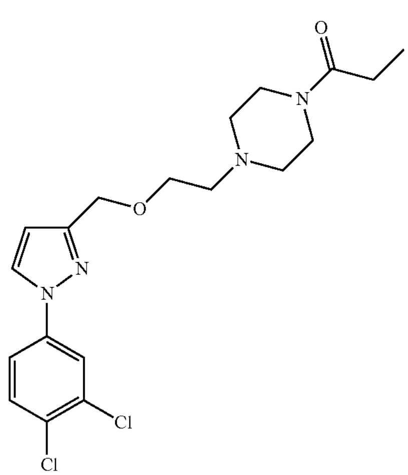 [SMILES: CCC(=O)N1CCN(CCOCc2ccn(-c3ccc(Cl)c(Cl)c3)n2)CC1] | 1-(4-(2-((1-(3,4-dichlorophenyl)-1H-pyrazol-3-yl)methoxy)ethyl)-piperazin-1-yl)-propan-1-one | |

| Example | Structure | Name | NMR |
|---|---|---|---|
| 50 | 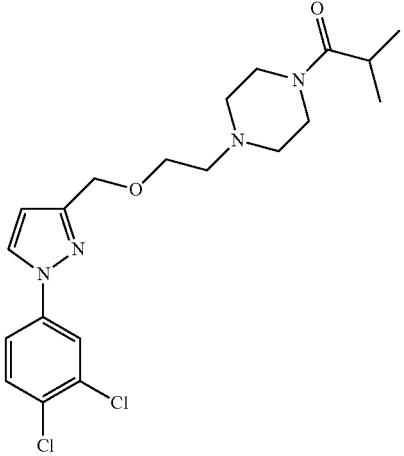 [SMILES: CC(C)C(=O)N1CCN(CCOCc2ccn(-c3ccc(Cl)c(Cl)c3)n2)CC1] | 1-(4-(2-((1-(3,4-dichlorophenyl)-1H-pyrazol-3-yl)methoxy)ethyl)-piperazin-1-yl)-2-methylpropan-1-one | |

BIOLOGICAL ACTIVITY

Some representative compounds of the invention were tested for their activity as sigma (sigma-1) inhibitors. The following protocol was followed:

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding was defined by addition of a final concentration of 1 μM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al, (1951).

REFERENCES

DeHaven-Hudkins, D. L., L. C. Fleissner, and F. Y. Ford-Rice, 1992, "Characterization of the binding of [$^3$H](+)pentazocine to a recognition sites in guinea pig brain", Eur. J. Pharmacol. 227, 371-378.

Lowry, O. H., N. J. Rosebrough, A. L. Farr, and R. J. Randall, 1951, Protein measurement with the Folin phenol reagent, J. Biol. Chem., 193, 265.

Some of the results obtained are shown in table (I).

TABLE (I)

| Compound | $K_i \sigma 1$ nM |
|---|---|
| 1 | 13.82 |
| 2 | 208.93 |
| 3 | 4.74 |
| 4 | 132.01 |
| 5 | 112.66 |
| 6 | 23.57 |
| 7 | 53.29 |
| 8 | 6.12 |
| 9 | 2.09 |
| 10 | 14.59 |
| 11 | 3.20 |
| 12 | 770.60 |
| 13 | 8.62 |
| 14 | 280.81 |
| 15 | 2.13 |
| 16 | 22.9 |
| 17 | 154.34 |
| 18 | 6.28 |
| 20 | 6.80 |
| 21 | 240.07 |
| 22 | 100.65 |
| 23 | 488.25 |
| 24 | 266.17 |
| 25 | 11.31 |
| 26 | 110.17 |

The invention claimed is:
1. A compound of general formula (I):

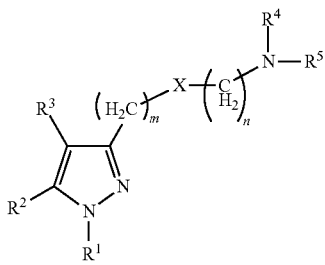

wherein
$R^1$ represents substituted or unsubstituted, aromatic or non-aromatic heterocyclyl; substituted or unsubstituted aryl; or substituted or unsubstituted cycloalkyl;
$R^2$ represents a hydrogen atom; F; Cl; Br; I; $CF_3$; OH; SH; CN; methyl; substituted or unsubstituted alkenyl; substituted or unsubstituted alkoxy; substituted or unsubstituted cycloalkyl; substituted or unsubstituted, non-aromatic heterocyclyl; substituted or unsubstituted cycloalkylalkyl; substituted or unsubstituted arylalkyl; substituted or unsubstituted, aromatic or non-aromatic heterocyclylalkyl; a (C=O)—$R^7$ group; a (C=O)—O—$R^8$ group; a $S(O)_t$—$R^9$ group; or a (C=O)—$NR^{10}R^{11}$ group;
$R^3$ represents a hydrogen atom; F; Cl; Br; I; $CF_3$; OH; SH; $NH_2$; CN; substituted or unsubstituted alkyl; substituted or unsubstituted alkenyl; substituted or unsubstituted alkoxy; substituted or unsubstituted cycloalkyl; substituted or unsubstituted aryl; substituted or unsubstituted, aromatic or non-aromatic heterocyclyl; substituted or unsubstituted cycloalkylalkyl; substituted or unsubstituted arylalkyl; substituted or unsubstituted, aromatic or non-aromatic heterocyclylalkyl; a (C=O)—$R^7$ group; a (C=O)—O—$R^8$ group; a $S(O)_t$—$R^9$ group; or a (C=O)—$NR^{10}R^{11}$ group;
$R^4$ and $R^5$ form, together with the nitrogen atom to which they are attached, a substituted or unsubstituted heterocyclyl group;
X represents an oxygen atom or a CH—$R^{12}$ group wherein $R^{12}$ is selected from H, $CH_3$, SH, OH, $NH_2$, $CF_3$, Cl, F, Br, I, and CN;
m is 1, 2, 3 or 4;
n is 1, 2, 3 or 4;
t is 1, 2 or 3; and
$R^7$, $R^8$, $R^9$, $R^{10}$ and $R^{11}$, identical or different, represent a hydrogen atom; substituted or unsubstituted $C_{1-6}$ alkyl; substituted or unsubstituted $C_{2-6}$ alkenyl; substituted or unsubstituted $C_{1-6}$ alkoxy; substituted or unsubstituted cycloalkyl; substituted or unsubstituted aryl; substituted or unsubstituted, aromatic or non-aromatic heterocyclyl; substituted or unsubstituted cycloalkylalkyl; substituted or unsubstituted arylalkyl; substituted or unsubstituted, aromatic or non-aromatic heterocyclylalkyl;
or a pharmaceutically acceptable salt, prodrug or solvate thereof.

2. The compound according to claim 1, wherein $R^1$ is a 5- to 10 membered substituted or unsubstituted, aromatic or non-aromatic heterocyclyl group which preferably contains N, O or S as ring member; a 5 to 10 membered substituted or unsubstituted aryl group; or a 5 to 10 membered substituted or unsubstituted cycloalkyl group.

3. The compound according to claim 2, wherein $R^1$ is substituted or unsubstituted cyclopentyl, substituted or unsubstituted cyclohexyl, substituted or unsubstituted phenyl, substituted or unsubstituted naphthyl, substituted or unsubstituted thiophene, substituted or unsubstituted benzothiophene, substituted or unsubstituted benzofuran, substituted or unsubstituted pyridine or substituted or unsubstituted quinoline.

4. The compound according to claim 3, wherein $R^1$ is selected from the group consisting of: 2-thienyl, 3-thienyl, 2,5-dichloro-3-thienyl, 2,3-dichloro-5-thienyl, 2,3-dichloro-4-thienyl, 2-benzothienyl, 3-benzothienyl, 4-benzothienyl, 5-benzothienyl, 7-benzothienyl, 2-benzofuryl, 5-benzofuryl, 2-pyridyl, 3-pyridyl, 4-pyridyl, 2-quinolyl, 3-quinolyl, 5-quinolyl, 6-quinolyl, 3,4-difluorophenyl, 3,4-dichlorophenyl, cyclopentyl, cyclohexyl, 7-hydroxy-2-naphthyl, 6-hydroxy-2-naphthyl, 5-hydroxy-2-naphthyl, 6-fluoro-2-naphthyl, 6-methoxy-2-naphthyl, 6-bromo-2-naphthyl, 6-hydroxymethyl-2-naphthyl, 6-fluromethyl-2-naphthyl, 7-hydroxy-1-naphthyl, 6-hydroxy-1-naphthyl, 5-hydroxy-1-naphthyl, 5-fluoro-1-naphthyl, 5-bromo-1-naphthyl and 1-naphthyl.

5. The compound according to claim 1, wherein $R^2$ is H or methyl and $R^3$ is H or substituted or unsubstituted $C_{1-6}$ alkyl group.

6. The compound according to claim 5, wherein $R^2$ is methyl and $R^3$ is H, or $R^2$ and $R^3$ are simultaneously H or methyl.

7. The compound according to claim 1, wherein $R^4$ and $R^5$ form together a morpholine-4-yl group, a piperidine group, pyrrolidine group or a piperazine-4-yl group.

8. The compound according to claim 1, wherein each m and n independently represent 1 or 2.

9. The compound according to claim 1 selected from the group consisting of:
4-(2-((1-(3,4-dichlorophenyl)-5-methyl-1H-pyrazol-3-yl)methoxy)ethyl)morpholine,
4-(2-((5-methyl-1-(naphthalen-2-yl)-1H-pyrazol-3-yl)methoxy)ethyl)morpholine,
4-(3-(1-(3,4-dichlorophenyl)-5-methyl-1H-pyrazol-3-yl)propyl)morpholine,
4-(3-(5-methyl-1-(naphthalen-2-yl)-1H-pyrazol-3-yl)propyl)morpholine,
4-(2-(2-(1-(3,4-dichlorophenyl)-5-methyl-1H-pyrazol-3-yl)ethoxy)ethyl)morpholine,
4-(2-((1-cyclohexyl-5-methyl-1H-pyrazol-3-yl)methoxy)ethyl)morpholine,
4-(3-(1-cyclohexyl-5-methyl-1H-pyrazol-3-yl)propyl)morpholine,
1-(3,4-dichlorophenyl)-5-methyl-3-((2-(pyrrolidin-1-yl)ethoxy)methyl)-1H-pyrazole,
1-(2-((1-(3,4-dichlorophenyl)-5-methyl-1H-pyrazol-3-yl)methoxy)ethyl)piperidine,
1-(4-(2-((1-(3,4-dichlorophenyl)-5-methyl-1H-pyrazol-3-yl)methoxy)ethyl)piperazin-1-yl)ethanone,
(2S,6R)-4-(2-((1-(3,4-dichlorophenyl)-5-methyl-1H-pyrazol-3-yl)methoxy)ethyl)-2,6-dimethylmorpholine,
4-(2-((5-methyl-1-(quinolin-3-yl)-1H-pyrazol-3-yl)methoxy)ethyl)morpholine,
4-(4-(1-(3,4-dichlorophenyl)-5-methyl-1H-pyrazol-3-yl)butyl)morpholine,
4-(3-(5-methyl-1-(quinolin-3-yl)-1H-pyrazol-3-yl)propyl)morpholine,
4-(2-((1-(3,4-dichlorophenyl)-1H-pyrazol-3-yl)methoxy)ethyl)morpholine,
4-(2-((1-(3,4-dichlorophenyl)-4,5-dimethyl-1H-pyrazol-3-yl)methoxy)ethyl)morpholine, 4-(3-(1-(quinolin-3-yl)-1H-pyrazol-3-yl)propyl)morpholine,
4-(4-(1-(3,4-dichlorophenyl)-1H-pyrazol-3-yl)butyl)morpholine,
4-(4-(5-methyl-1-(quinolin-3-yl)-1H-pyrazol-3-yl)butyl) morpholine,
4-(3-((1-cyclohexyl-5-methyl-1H-pyrazol-3-yl)methoxy)propyl)morpholine,
4-(2-((1-cyclopentyl-5-methyl-1H-pyrazol-3-yl)methoxy)ethyl)morpholine,
1-(4-(2-((1-cyclohexyl-5-methyl-1H-pyrazol-3-yl)methoxy)ethyl)piperazin-1-yl)ethanone hydrochloride,
(3S,5R)-1-(2-((1-cyclohexyl-5-methyl-1H-pyrazol-3-yl)methoxy)ethyl)-3,5-dimethylpiperazine hydrochloride,
4-(2-(2-(1-cyclohexyl-5-methyl-1H-pyrazol-3-yl)ethoxy) ethyl)morpholine hydrochloride,
4-(2-((1-cyclohexyl-1H-pyrazol-3-yl)methoxy)ethyl) morpholine hydrochloride,
4-(2-((1-cyclohexyl-4,5-dimethyl-1H-pyrazol-3-yl)methoxy)ethyl)morpholine hydrochloride,
1-(4-(2-((1-cyclohexyl-1H-pyrazol-3-yl)methoxy)ethyl) piperazin-1-yl)ethanone,
1-(4-(3-((1-cyclohexyl-1H-pyrazol-3-yl)methoxy)propyl) piperazin-1-yl)ethanone,
1-(4-(4-((1-cyclohexyl-1H-pyrazol-3-yl)methoxy)butyl) piperazin-1-yl)ethanone,
1-(4-(4-((1-cyclohexyl-5-methyl-1H-pyrazol-3-yl)methoxy)butyl)piperazin-1-yl)ethanone,
1-(4-(3-((1-cyclohexyl-5-methyl-1H-pyrazol-3-yl)methoxy)propyl)piperazin-1-yl)ethanone,
1-(4-(2-((1-(3,4-dichlorophenyl)-1H-pyrazol-3-yl)methoxy)ethyl)piperazin-1-yl)ethanone
1-(4-(3-((1-(3,4-dichlorophenyl)-1H-pyrazol-3-yl)methoxy)propyl)piperazin-1-yl)ethanone,
1-(4-(4-((1-(3,4-dichlorophenyl)-1H-pyrazol-3-yl)methoxy)butyl)piperazin-1-yl)ethanone,
1-(4-(3-((1-(3,4-dichlorophenyl)-5-methyl-1H-pyrazol-3-yl)methoxy)propyl)piperazin-1-yl)ethanone,
1-(4-(3-((1-(3,4-difluorophenyl)-1H-pyrazol-3-yl)methoxy)propyl)piperazin-1-yl)ethanone,
1-(4-(3-((1-(3,4-difluorophenyl)-5-methyl-1H-pyrazol-3-yl)methoxy)propyl)piperazin-1-yl)ethanone,
1-(4-(2-((1-(3,4-difluorophenyl)-5-methyl-1H-pyrazol-3-yl)methoxy)ethyl)piperazin-1-yl)ethanone,
1-(4-(2-((1-(3,4-difluorophenyl)-1H-pyrazol-3-yl)methoxy)ethyl)piperazin-1-yl)ethanone,
4-(2-((1-(3,4-difluorophenyl)-5-methyl-1H-pyrazol-3-yl) methoxy)ethyl)morpholine,
4-(2-((1-(3,4-difluorophenyl)-1H-pyrazol-3-yl)methoxy) ethyl)morpholine,
4-(3-((1-(3,4-difluorophenyl)-5-methyl-1H-pyrazol-3-yl) methoxy)propyl)morpholine,
1-(4-(2-((1-cyclohexyl-5-methyl-1H-pyrazol-3-yl)methoxy)ethyl)piperazin-1-yl)propan-1-one,
1-(4-(2-((1-cyclohexyl-5-methyl-1H-pyrazol-3-yl)methoxy)ethyl)piperazin-1-yl)-2-methylpropan-1-one,
1-(4-(2-((1-cyclohexyl-1H-pyrazol-3-yl)methoxy)ethyl) piperazin-1-yl)propan-1-one,
1-(4-(2-((1-cyclohexyl-1H-pyrazol-3-yl)methoxy)ethyl) piperazin-1-yl)-2-methylpropan-1-one,
1-(4-(2-((1-(3,4-dichlorophenyl)-5-methyl-1H-pyrazol-3-yl)methoxy)ethyl)piperazin-1-yl)propan-1-one,
1-(4-(2-((1-(3,4-dichlorophenyl)-5-methyl-1H-pyrazol-3-yl)methoxy)ethyl)piperazin-1-yl)-2-methylpropan-1-one,
1-(4-(2-((1-(3,4-dichlorophenyl)-1H-pyrazol-3-yl)methoxy)ethyl)piperazin-1-yl)propan-1-one, and
1-(4-(2-((1-(3,4-dichlorophenyl)-1H-pyrazol-3-yl)methoxy)ethyl)piperazin-1-yl)-2-methylpropan-1-one, or a pharmaceutically acceptable salt, prodrug or solvate thereof.

10. A process for the preparation of a compound of formula (I) as defined in claim 1, or a salt, isomer or solvate thereof, which is:

a) a process which comprises the reaction of a compound of formula (II)

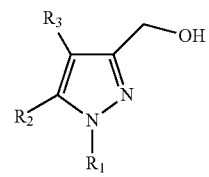

(II)

with a compound of formula (III)

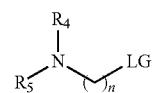

(III)

in which LG represents a leaving group;

b) a process which comprises the oxidation of a compound of formula (II) to afford a compound of formula (VII)

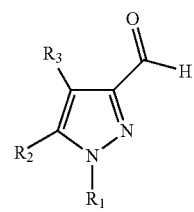

(VII)

followed by the reaction of the compound of formula (VII) with a phosphonium salt of formula (VIII)

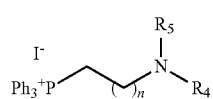

(VIII)

to afford a compound of formula (IX)

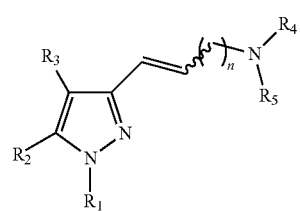

(IX)

and reduction of the compound of formula (IX);

c) a process which comprises the oxidation of a compound of formula (II) to afford a compound of formula (VII)

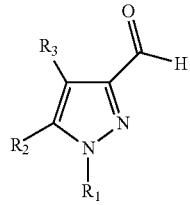
(VII)

followed by the reaction of the compound of formula (VII) with a suitable phosphonium salt and subsequent acid hydrolysis to afford a compound of formula (XI)

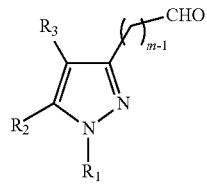
(XI)

reduction of the compound of formula (XI) and subsequent reaction with a compound of formula (III)

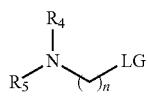
(III)

in which LG represents a leaving group;

d) a process which comprises reaction of 3-acetyl-6-methyl-pyran-2,4-dione with magnesium and subsequent reaction with a compound of formula (V):

(V)

to afford a compound of formula (XV)

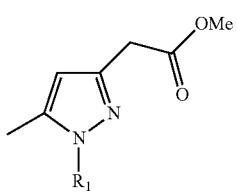
(XV)

and reduction of the compound of formula (XV) and subsequent reaction with a compound of formula (III)

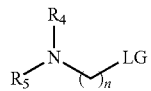
(III)

in which LG represents a leaving group;

e) a process which comprises the oxidation of a compound of formula (II) to afford a compound of formula (VII)

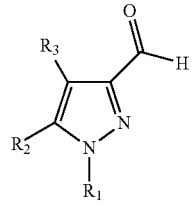
(VII)

followed by the reaction of the compound of formula (VII) with a phosphonium salt of formula (XVII)

(XVII)

to afford a compound of formula (XVII)

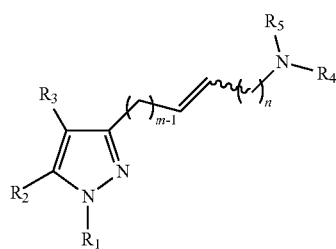
(XVIII)

and reduction of the compound of formula (XVIII).

11. A medicament comprising at least one compound of formula (I) as defined in any of claim 1, or a pharmaceutically acceptable salt, prodrug or solvate thereof and a pharmaceutically acceptable excipient.

12. A method for the manufacture of a medicament comprising combining the compound as defined in claim 1 with a pharmaceutically acceptable excipient.

13. A method for the treatment of a sigma receptor-mediated disease or condition, comprising administering to a patient a therapeutically amount of the compound as defined in claim 1.

14. The method according to claim 13, wherein the disease comprises diarrhea; lipoprotein disorders; migraine; obesity; elevated triglyceride levels; chylomicronemia; dysbetalipoproteinemia; hyperlipoproteinemia; hyperlipidemia; mixed hyperlipidemia; hypercholesterolemia; hypertriglyceridemia; sporadic hypertriglyceridemia; inherited hypertriglyceridemia; arthritis; hypertension; arrhythmia; ulcer; demyelinating diseases; addiction to drugs and chemical substances including cocaine, amphetamine, ethanol and nicotine; tardive dyskinesia; ischemic stroke; epilepsy; stroke; stress; psychotic conditions; or inflammation.

15. The method according to claim 13, wherein the disease is pain.

16. Compound of general formula (I) as defined in claim 1 for use as a pharmacological tool.

17. The method according to claim 13, wherein the disease is depression, anxiety or schizophrenia.

18. The method according to claim 15, wherein the pain is neuropathic pain, inflammatory pain or other pain conditions involving allodynia and/or hyperalgesia.

19. The compound according to claim 5, wherein $R^2$ and $R^3$ are independently H or methyl.

* * * * *